United States Patent
Woodward

(10) Patent No.: US 11,013,822 B1
(45) Date of Patent: May 25, 2021

(54) SMALLEST PARTICULATE ABSORBER

(71) Applicant: Malcolm Philemon Woodward, Charlottesville, VA (US)

(72) Inventor: Malcolm Philemon Woodward, Charlottesville, VA (US)

( * ) Notice: Subject to any disclaimer, the term of this patent is extended or adjusted under 35 U.S.C. 154(b) by 0 days.

(21) Appl. No.: 15/930,062

(22) Filed: May 12, 2020

(51) Int. Cl.
  *B01D 53/02* (2006.01)
  *A61L 9/20* (2006.01)
  *A61L 2/20* (2006.01)
  *A61L 2/08* (2006.01)
  *F24F 8/10* (2021.01)
  *F24F 8/22* (2021.01)

(52) U.S. Cl.
  CPC ............... *A61L 9/20* (2013.01); *A61L 2/087* (2013.01); *A61L 2/202* (2013.01); *F24F 8/10* (2021.01); *A61L 2209/12* (2013.01); *F24F 8/22* (2021.01)

(58) Field of Classification Search
  CPC . A61L 9/20; A61L 2/087; A61L 2/202; A61L 2209/12; F24F 3/1603; F24F 2003/1667
  See application file for complete search history.

(56) References Cited

U.S. PATENT DOCUMENTS

| | | | | |
|---|---|---|---|---|
| 5,107,687 A * | 4/1992 | Candeloro | ............... | F24F 3/08 165/48.1 |
| 5,200,156 A * | 4/1993 | Wedekamp | ............... | A61L 2/10 313/493 |
| 5,330,722 A * | 7/1994 | Pick | ............... | A61L 9/20 96/55 |
| 5,523,057 A * | 6/1996 | Mazzilli | ............... | A61L 9/20 250/436 |
| 5,612,001 A * | 3/1997 | Matschke | ............... | A61L 2/10 250/455.11 |
| 5,635,133 A * | 6/1997 | Glazman | ............... | A61L 2/10 422/24 |
| 6,022,511 A * | 2/2000 | Matschke | ............... | A61L 9/20 250/436 |
| 6,228,327 B1 * | 5/2001 | Matschke | ............... | A61L 9/20 250/436 |
| 7,625,277 B2 * | 12/2009 | Palmer | ............... | F24F 11/77 454/255 |
| 7,875,247 B2 * | 1/2011 | Clark | ............... | A61L 9/205 422/121 |
| 10,451,298 B2 * | 10/2019 | Matschke | ............... | F24F 8/192 |
| 2016/0001108 A1 * | 1/2016 | Zhou | ............... | A61L 9/00 128/863 |
| 2016/0231018 A1 * | 8/2016 | Green | ............... | F24F 13/0227 |
| 2019/0120522 A1 * | 4/2019 | Green | ............... | F24F 13/28 |
| 2020/0345885 A1 * | 11/2020 | Lewis | ............... | A61L 9/127 |

* cited by examiner

*Primary Examiner* — Christopher P Jones

(57) ABSTRACT

This invention is designed to neutralize and destroy all airborne particulates and infectious material prior to the return of this ventilation air into the High Energy Particulate Absorber [HEPA] System of a forced air ventilation building. This sterilizing and purifying device will return only safe and clean air to the building ventilation system. This smallest particulate absorber will be located just prior to the standard return air vent in the forced air ventilation system and it will neutralize and destroy all sizes, even nano and micro sized airborne particulates.

10 Claims, 8 Drawing Sheets

Front View

PRIOR ART

RESEARCHERS MAP WHERE HOSPITAL PATHOGENS ARE LURKING

The Wall Street Journal, April 28, 2015

An Article Written By Robert Lee Hotz concerning results from a three year Hospital Microbiome Project

PRIOR ART

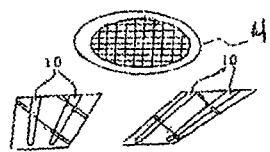
FIGURE 6
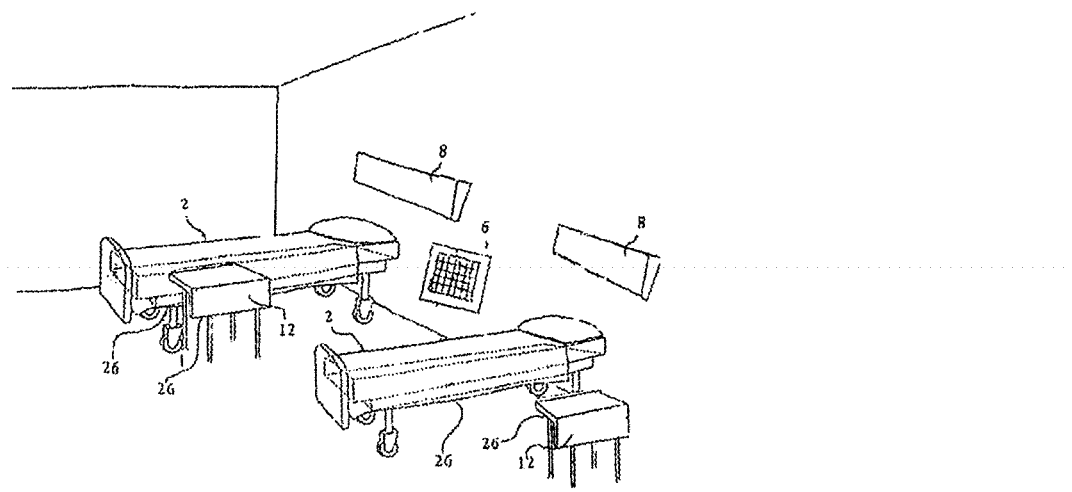
FIGURE 7
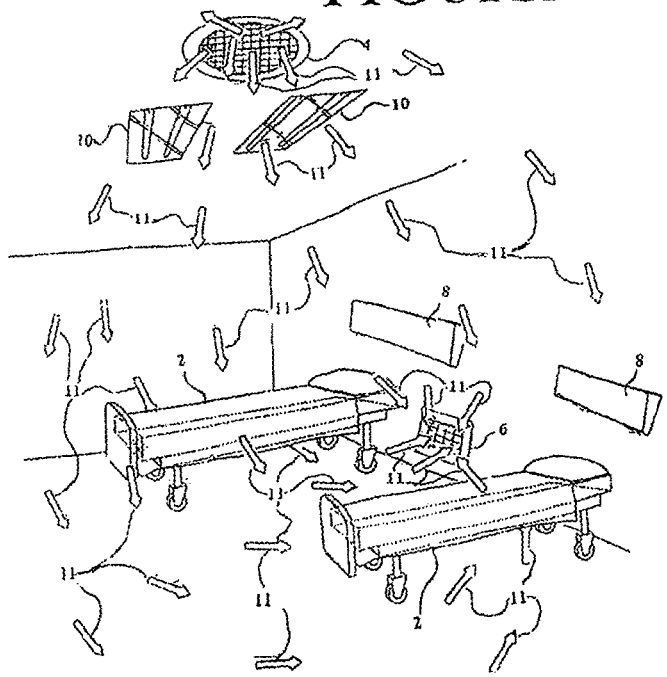

Front View

Rear View

SMALLEST PARTICULATE ABSORBER

This U.S. Patent in Application as a Non Provisional Patent [NPA] claims Entire Priority Benefit of a timely filed Provisional Patent [PPA] #62/920,807, filed May 17, 2019, entitled "Smallest Particulate Absorber" in its Confirmation No. 9832 from THE USPTO.

FIELD OF SEARCH:

BY INTERNATIONAL CLASSES:

| | | |
|---|---|---|
| A61L | 2/00 | [2006.01] |
| A01L | 2/10 | [2006.01] |
| A61L | 2/205 | [2006.01] |
| A61L | 2/208 | [2006.01] |
| A61L | 2/218 | [2006.01] |
| A61L | 2/20 | [2006.01] |
| A61L | 9/00 | [2006.01] |
| A61L | 9/20 | [2006.01] |
| A61M | 5/3202 | [2006.01] |
| A61M | 5/3278 | [2006.01] |
| A61N | 5/00 | [2006.01] |
| B01D | 27/00 | [2006.01] |
| B01D | 39/00 | [2006.01] |
| B01D | 46/00 | [2006.01] |
| B01D | 53/00 | [2006.01] |
| B01D | 53/82 | [2006.01] |
| B65D | 81/00 | [2006.01] |
| G01N | 1/00 | [2006.01] |
| G01N | 1/28 | [2006.01] |
| G01N | 3/00 | [2006.01] |
| G01N | 5/08 | [2006.01] |
| G01N | 15/06 | [2006.01] |
| G01N | 21/01 | [2006.01] |
| H01J | 5/56 | [2006.01] |
| H01J | 37/00 | [2006.01] |
| H01J | 61/00 | [2006.01] |
| H01J | 61/00 | [2006.01] |

U. S. CLASSES:
CPC:
A01G 1/00 [2006.01];
A01N 55/00 [2006.01];
A23B 4/015 [2006.01];
A23L 3/00 [2006.01], 3/28 [2006.01];
A45C 5/0 [2013.01];
A61B 5/08 [2006.01], 5/082 [2013.01], 5/097 [2013.01], 17/42 [2006.01 & 2013.01], 17/43 [2006.01 & 2013.01], 50/00 [2016.01], 50/36 [2016.01], 50/364 [2016.02];
A61F 7/00 [2006.01];
A61K 1/40 [2013.01], 9/70 [2006.01], 9/7015 [2013.01], 31/695 [2006.01], 38/00 [2006.01], 45/06 [2006.01 & 2013.01];
A61L 2/00 [2006.01 & 2013.01], 2/02 [2006.01], 2/022 [2013.01], 2/10 [2006.01], 2/16 [2013.01], 2/18 [2006.01], 2/22 [2013.01], 2/24 [2006.01& 2013.01], 2/186 [2013.01], 2/202 [2013.01], 9/00 [2006.01 & 2013.01], 9/015 [2006.01], 9/04 [2013.01], 9/12 [2006.01], 9/20[2006.01& 2013.01], 9/205 [2013.01], 13/00 [2006.01];
A61M 5/3202 [2006.01], 5/3278 [2006.01];
A61N 5/00 [2006.01];
A62B 7/08 [2006.01], 9/00 [2006.01], 18/08 [2006.01];
A61C 13/62 [2006.01];
B01D 27/00 [2006.01], 29/11 [2006.01], 35/14 [2006.01], 39/00 [2013.01], 39/1607 2013.01], 46/00 [2006.01], 46/30 [2006.01], 46/38 [2006.01], 46/46 [2006.01], 46/52 [2006.01], 53/00 [2006.01 & 2013.01], 53/02 [2006.01 & 2013.01], 53/04 [2013.01], 53/007 [2013.01], 53/22 [2006.01], 53/32 [2013.01], 53/34 [2013.01], 53/38 [2013.01], 53/44 [2006.01], 53/46 [2006.01], 53/72 [2006.01], 53/75 [2006.01], 53/82 [2006.01], 53/228 [2013.01]; 53/348 [2013.01], 53/407 [2013.01], 53/454 [2013.01], 46/521 [2013.01], 85/00 [2006.01];
B01L 1/04 [2006.01];
B01J 1/10 [2006.01], 19/00 [2006.01], 19/08 [2006.01], 19/12 [2006.01] 23/00 [2006.01];
B03C 1/30 [2013.01], 3/09 [2013.01], 3/011 [2006.01], 3/025 [2013.01], 3/36 [2006.01], 3/64 [2006.01], 3/361 [2013.01];
B05D 3/02 [2006.01], 3/06 [2006.01];
B08B 15/00 [2006.01];
B29B 64/00 [2017.01], 64/106 [2017.01], 64/141 [2017.01];
B41M 7/00 [2006.01];
B65B 1/04 [2006.01 & 2013.01], 1/06 [2013.01], 1/16 [2013.01], 1/28 [2013.01], 23/00 [2006.01], 55/02 [200.6.01], 55/08 [2006.01];
B65D 41/00 [2006.01], 69/00 [2006.01], 81/00 [2006.01], 81/24 [2006.01], 83/10 [2006.01], 85/00 [2006.01];
B65G 67/00 [2006.01];
C07K 1/22 [2013.01], 1/34 [2006.01], 14/775 [2006.01], 16/06 [2006.01], 16/18 [2006.01], 19/00 [2006.01];
C08K 5/00 [2006.01];
C12N 5/0604 [2013.01], 5/073 [2010.01], 7/02 [2006.01], 13/00 [2006.01];
C12M 1/00 [2006.01], 1/12 [2006.01], 1/28 [2006.01], 1/34 [2006.01];
C12Q 1/24 [2006.01], 1/68 [2006.01], 1/689 [2013.01];
C25C 7/00 [2006.01];
F24F 3/16 [2006.01], 3/161 [2013.01], 7/00 [2006.01], 11/00 [2018.01]; 11/30 [2018.01], 11/75 [2018.01], 11/77 [2018.01], 13/10 [2018.01];
F25B 29/00 [2006.01];
G01J 1/00 [2006.01], 1/34 [2006.01], 1/42 [2006.01], 3/10 [2006.01];
G01L 7/08 [2006.01];
G01N 1/00 [2006.01], 1/22 [2006.01], 1/28 [2006.01], 1/2208 [2013.01], 3/00 [2006.01], 03/68 [2013.01], 5/08 [2006.01], 9/30 [2006.01], 5/96 [2013.01], 15/06 [2006.01], 15/0612 [2013.01], 21/01 [2006.01], 21/06 [2006.01], 21/45 [2006.01], 21/47 [2006.01], 21/58 [2013.01], 21/94 [2013.01], 21/4738 [2013.01], 23/00 [2006.01], 23/10 [2006.01], 24/08 [2006.01], 24/084 [2013.01], 24/85 [2013.01], 27/26 [2006.01], 33/00 [2006.01], 33/0062 [2013.01];
G01V 3/00 (2006.01], 8/00 [2006.01];
G01W 1/00 [2006.01];
G05B 19/00 [2006.01];
G05D 7/00 [2006.01], 99/00 [2006.01];
G08B 21/00 [2006.01], 21/18 [2006.01]; G21K 5/08 [2006.01];
H01J 5/56 [2006.01], 11/00 [2012.01], 17/20 [2012.01], 17/30 [2006.01], 37/00 [2006.01], 49/26 [2006.01], 61/00 [2006.01], 61/02 [2006.01], 61/025 [2013.01], 61/20 [2006.01], 63/08 [2006.01];
H01S 3/30 [2006.01];
H05B 31/00 [2006.01];
H05G 2/00 [2006.01];
H05H 1/10 [2006.01], 1/24 [2006.01];
H05K 3/00 [2006.01];
USPC:
42/255, 292, 301,
55/210
73/336.5
95/47

128/396
204/275;
206/210, 364-5, 370, 454, 568;
USPC Continued:
210/87, 497.3, 604;
236/44, 49.3;
241/33, 36, 46.017;
250/222.2, 282, 372, 430, 432, 436, 453.11, 454.11, 455.11, 461.1, 492.1, 493, 503.1, 504;
313/238, 574, 634, 639;
315/111.7;
324/309;
340/539.1, 607, 628;
372/5;
422/3, 4, 5, 22, 24, 28, 62, 105, 108, 116, 121, 171, 185, 186.15, 186.3, 295;
435/6, 30, 173.3, 294;
436/174;
454/229;
516/98;
524/349;
588/313;
604/110, 192, 199; 408;
606/10;
607/92;
700/276.

REFERENCES CITED:
U.S. PATENT DOCUMENTS:

| Number | Date | Name | Class | |
|---|---|---|---|---|
| 364,579A | June 1887 | Dahl | A23C 3/033 | ++ |
| 1,676,579A | July 1923 | Sperti | C12N 13/00 | ++ |
| 1,723,188A | August 1929 | Manchester | A23C 9/1516 | + |
| 1,980,971A | November 1934 | Campsie | A23L 3/28 | + |
| 2,072,417A | March 1937 | Berndt | A23L 3/28 | + |
| 2,169,081A | August 1939 | James | A23B 4/015 | + |
| 2,258,765A | October 1941 | James | A23L 3/28 | + |
| 2,261,215A | November 1941 | Bird | A61N 5/0616 | +++ |
| 2,265,252A | December 1941 | Shaefer | A61L 9/20 | ++ |
| 2,282,507A | September 1949 | Rentschler et al | A23C 3/07 | +++ |
| 2,284,551A | May 1942 | Alexander | B65B 31/025 | x |
| 2,348,617A | May 1944 | Furedy | A61N 5/06 | + |
| 2,449,681A | September 1948 | Wilson | F24F 3/16 | + |
| 2,482,507A | September 1949 | Rentsschler | A23C 3/07 | +++ |
| 2,533,339A | December 1950 | Willenborg | G01N 27/16 | x |
| 2,611,679A | September 1952 | Hanlenbeek et al | A47L 7/04 | + |
| 2,628,083A | February 1953 | Rense | F24F 3/12 | + |
| 2,638,644A | May 1953 | Rauhut | F24F 6/043 | x |
| 2,753,831A | July 1956 | Davies | B01D 46/10 | + |
| 2,804,839A | November 1957 | Hallinan | B01D 46/02 | ++ |
| 2,977,508A | March 1961 | Germeshausen | H01J 17/00 | + |
| 3,019,127A | January 1962 | Czerwonka et al/ | B01D 39/00 | + |
| 3,212,537A | October 1965 | Hinxlage et al | B67C 3/10 | + |
| 3,218,510A | November 1965 | Schulz | H01J 61/86 | +++ |
| 3,237,375A | March 1966 | Schwarz et al | B03C 3/011 | ++ |
| 3,350,602A | October 1967 | Germeshausen | H01J 17/44 | ++ |
| 3,410,055A | November 1968 | Zenz | B01D 46/30 | + |
| 3,418,069A | December 1968 | Decupper | A61L 9/20 | +++ |
| 3,456,107A | July 1969 | Robertson | A61L 2/10 | + |
| 3,458,130A | July 1969 | Juhlin | B01D 46/10 | + |
| 3,509,697A | May 1970 | Dewey et al | F24F 3/1603 | x |
| 3,516,232A | June 1970 | Gilbertson | A24F 19/0042 | x |
| 3,538,961A | November 1970 | Bruce | B60H 1/00585 | x |
| 3,660,651A | May 1972 | Miles, Jr | F21S 8/026 | x |
| 3,667,134A | June 1972 | Rockson | F26B 19/00 | + |
| 3,712,984A | January 1973 | Lienhard | A61C 19/004 | +++ |
| 3,753,651A | August 1973 | Boucher | A61I 1/00 | ++ |
| 3,795,135A | March 1974 | Anderson | G01N 15/06 | ++ |
| 3,804,942A | April 1974 | Kato et al | A47L 9/122 | ++ |
| 3,868,513A | February 1975 | Gonser | H01J 37/00 | +++ |
| 3,911,318A | October 1975 | Spero et al | H01J 7/46 | ++ |
| 3,926,556A | December 1975 | Boucher | A61L 13/00 | +++ |

-continued
REFERENCES CITED:
U.S. PATENT DOCUMENTS:

| Number | Date | Name | Class | |
|---|---|---|---|---|
| 3,937,667A | February 1976 | Scott | C22B 3/0097 | + |
| 3,937,915A | February 1976 | Matsuo et al | B23P 1/00 | x |
| 3,970,856A | July 1976 | Mahaffey et al | G01J 1/00 | ++ |
| 3,973,927A | August 1976 | Furchner | B03 3/68 | ++ |
| 3,984,296A | October 1976 | Richards | B01J 1/10 | ++ |
| 4,013,552A | March 1977 | Kreuter | C02C 1/02 | + |
| 4,063,890A | December 1977 | Baron | A61L 13/00 | ++ |
| 4,071,334A | January 1978 | Kolb et al | B03C 1/00 | ++ |
| 4,100,418A | July 1978 | Brown, Jr | G21K 3/00 | + |
| 4,102,654A | July 1978 | Pellin | B03C 3/38 | ++ |
| 4,119,419A | October 1978 | Passaro et al | B01D 46/46 | x |
| 4,141,830A | February 1979 | Last | C02B 1/38 | ++ |
| 4,149,086A | April 1979 | Nath | C01J 1/00 | ++ |
| 4,152,625A | May 1979 | Conrad | H05H 1/10 | ++ |
| 4,177,045A | December 1979 | Orel | B03C 3/36 | x |
| 4,180,850A | December 1979 | Bivens | F21V 19/02 | x |
| 4,214,962A | July 1980 | Pincon | A61L 1/00 | + |
| 4,229,658A | October 1980 | Gonser | G01J 1/00 | +++ |
| 4,282,863A | August 1981 | Beigler et al | A61B 19/00 | x |
| 4,304,996A | December 1981 | Blades | G01J 1/42 | x |
| 4,309,388A | July 1982 | Tenney et al | A61L 2/10 | + |
| 4,309,992A | January 1982 | Dodak et al | A61L 2/16 | ++ |
| 4,328,632A | October 1982 | Beers | F41C 31/00 | x |
| 4,336,223A | June 1982 | Hillman | A61L 2/10 | +++ |
| 4,392,187A | July 1983 | Bornhorst | F21P 3/00 | + |
| 4,427,636A | January 1984 | Obenshain | C01B 13/00 | ++ |
| 4,437,954A | March 1984 | Sammells et al | C25B 1/04 | + |
| 4,438,337A | March 1984 | Forrat | G01N 21/01 | +++ |
| 4,448,750A | May 1984 | Fuesting | A61L 2/10 | ++ |
| 4,464,336A | August 1984 | Hiramoto | A61L 2/10 | +++ |
| 4,469,835A | September 1984 | Laurin | C08K 5/00 | +++ |
| 4,500,327A | February 1985 | Nishino et al | B01D 53/04 | + |
| 4,504,445A | March 1985 | Walz | B01J 1/10 | +++ |
| 4,526,034A | July 1985 | Campbell et al | G01W 1/00 | +++ |
| 4,540,416A | September 1985 | Hattori et al | B65B 25/00 | x |
| 4,551,628A | November 1985 | Grossman | G01N 21/24 | ++ |
| 4,554,719A | November 1985 | Lewis | B23P 15/26 | ++ |
| 4,606,229A | August 1986 | Spence | G01L 7/08 | +++ |
| 4,629,658A | December 1986 | Lucas | B32B 27/08 | x |
| 4,636,405A | January 1987 | Mensah et al | B05D 3/06 | x |
| 4,646,215A | February 1987 | Levin et al | F21M 3/18 | x |
| 4,657,540A | April 1987 | Iwamoto et al | A61B 19/00 | + |
| 4,663,293A | May 1987 | Hempel et al | C12M 1/28 | ++ |
| 4,761,074A | August 1988 | Kohsaka et al | G01N 21/01 | + |
| 4,762,613A | July 1988 | Snowball | C02F 1/32 | ++ |
| 4,769,131A | September 1988 | Noll et al | C02F 1/32 | ++ |
| 4,790,862A | December 1988 | Naruo | B01D 46/46 | +++ |
| 4,798,702A | January 1989 | Tucker | G01N 23/10 | +++ |
| 4,812,263A | March 1989 | Login | C07C 85/00 | x |
| 4,816,307A | March 1989 | Honeycutt | B65B 85/24 | + |
| 4,837,484A | June 1989 | Elliasson | H01J 17/16 | ++ |
| 4,866,282A | September 1989 | Miripol et al | A61K 35/14 | x |
| 4,871,559A | October 1989 | Dunn et al | A23L 3/00 | x |
| 4,880,512A | November 1989 | Cornelius | B01J 19/08 | + |
| 4,884,896A | December 1989 | Conway | G01J 5/10 | + |
| 4,892,712A | January 1990 | Robertson et al | B01J 1/10 | + |
| 4,910,942A | March 1990 | Dunn | B65B 55/08 | x |
| 4,917,862A | April 1990 | Kraw et al | A61L 9/00 | +++ |
| 4,932,831A | June 1990 | White et al | B66C 9/00 | x |
| 4,938,404A | July 1990 | Helms et al | B65H 23/00 | + |
| 4,952,812A | August 1990 | Miripol et al | A61N 5/06 | ++ |
| 4,966,759A | October 1990 | Robertson et al | B01J 19/08 | x |
| 4,974,134A | November 1990 | Bourne | F21V 21/22 | x |
| 4,984,139A | January 1991 | Goggia | F21V 21/22 | x |
| 5,003,441A | March 1991 | Crowe et al | F21L 7/00 | x |
| 5,038,929A | August 1991 | Kubofeik | B65D 81/00 | +++ |
| 5,047,224A | September 1991 | Dhooge | C01B 31/20 | + |
| 5,114,070A | May 1992 | Lilja | G05D 15/00 | ++ |
| 5,120,409A | June 1992 | Hanulik | B29B 17/02 | ++ |
| 5,122,126A | June 1992 | Sakakiyama | B65D 33/16 | + |
| 5,124,957A | June 1992 | Owens et al | G04F 8/00 | x |
| 5,129,894A | July 1992 | Summermeyer et al | B65D 30/08 | + |
| 5,130,916A | July 1992 | Toth | F21V 21/22 | x |
| 5,144,146A | September 1992 | Wekhof | A61L 2/10 | +++ |
| 5,144,542A | September 1992 | Puglisi | F21S 1/00 | x |

REFERENCES CITED:
U.S. PATENT DOCUMENTS:

| | | | | |
|---|---|---|---|---|
| 5,145,063A | September 1992 | Lee | A61B 50/362 | ++ |
| 5,148,091A | September 1992 | Lagercrantz | G05B 19/10 | x |
| 5,148,710A | September 1992 | Gudehus et al | G01N 25/68 | x |
| 5,150,705A | September 1992 | Stinson | A61N 5/00 | + |
| 5,173,638A | September 1992 | Eliasson | H01J 17/16 | + |
| 5,221,387A | June 1993 | Robbins et al | B32B 31/26 | + |
| 5,233,723A | August 1993 | Hung | A47L 9/00 | ++ |
| 5,260,036A | November 1993 | Weigold et al | B01J 20/02 | + |
| 5,261,596A | November 1993 | Tachibana et al | F24F 7/00 | ++ |
| 5,271,892A | December 1993 | Hanson | A61L 2/26 | ++ |
| 5,279,609A | January 1994 | Meckler | F25D 17/08 | + |
| 5,292,280A | March 1994 | Janu et al | F24F 11/00 | + |
| 5,292,350A | March 1994 | Molock | G02C 7/04 | x |
| 5,304,584A | April 1994 | Nunez | C08F 24/00 | x |
| 5,324,233A | June 1994 | Owensby et al | B31B 1/84 | x |
| 5,333,511A | August 1994 | Boyum et al | G01N 1/24 | + |
| 5,350,033A | September 1994 | Kraft | B62D 1/28 | + |
| 5,372,252A | October 2003 | Alexander | B65D 81/22 | ++ |
| 5,373,430A | December 1994 | McDermott | F21V 7/00 | + |
| 5,394,934A | March 1995 | Rein et al | F25B 29/00 | ++ |
| 5,397,552A | March 1995 | Weigold et al | C02F 1/32 | + |
| 5,398,026A | March 1995 | Hanhsaker | G08B 23/00 | x |
| 5,399,267A | March 1995 | Wang | B09C 1/02 | ++ |
| 5,428,964A | July 1995 | Lobdell | F24F 3/16 | ++ |
| 5,433,738A | July 1995 | Stinson | A61N 5/06 | ++ |
| 5,434,419A | July 1995 | Decupper | G01J 3/02 | +++ |
| 5,441,622A | August 1995 | Langford | C25C 7/00 | +++ |
| 5,456,740A | October 1995 | Snow | B01D 71/02 | ++ |
| 5,461,368A | October 1995 | Comer | G08B 21/00 | ++ |
| 5,484,863A | January 1996 | Molock | C08F 226/02 | + |
| 5,494,155A | February 1996 | Evans et al | B65D 81/22 | + |
| 5,500,369A | March 1996 | Kiplinger | G01N 5/02 | + |
| 5,511,106A | April 1996 | Doebert et al | A61B 6/03 | + |
| 5,513,085A | April 1996 | Bourne | F21V 21/22 | x |
| 5,520,328A | May 1996 | Bujak, Jr | F25B 29/00 | ++ |
| 5,538,697A | July 1996 | Abe et al | B01D 53/34 | + |
| 5,540,266A | July 1996 | Grau et al | F16L 37/28 | + |
| 5,550,727A | August 1996 | Fenyvesy | B60Q 1/06 | x |
| 5,570,992A | November 1996 | Lemelson | B66C 23/00 | x |
| 5,581,152A | December 1996 | Matsumo et al | H01J 61/067 | + |
| 5,586,748A | December 1996 | Kish | F16L 37/28 | x |
| 5,589,824A | December 1996 | Lynch | G08B 17/10 | ++ |
| 5,628,558A | May 1997 | Iacono et at | F21V 19/02 | x |
| 5,643,464A | July 1997 | Rhee | B01J 1/06 | x |
| 5,652,339A | July 1997 | Lerch | C07K 1/00 | + |
| 5,654,350A | August 1997 | Nunez et al | G02C 7/04 | x |
| 5,667,564A | September 1997 | Weinberg | A61L 9/22 | ++ |
| 5,681,871A | October 1997 | Molock | C08L 33/04 | + |
| 5,684,058A | November 1997 | Nunez | C08F 24/00 | + |
| 5,689,364A | November 1997 | McGregor et al | G02B 5/08 | + |
| 5,718,270A | February 1998 | Grau et al | F16L 37/28 | x |
| 5,733,021A | March 1998 | O'Neill et al | A47F 3/00 | x |
| 5,758,775A | June 1998 | Lowe | A61C 5/3205 | ++ |
| 5,766,958A | June 1998 | Sullivan et al | G01N 1/28 | ++ |
| 5,768,853A | June 1998 | Bushnell et al | B65B 55/00 | + |
| 5,786,525A | July 1998 | Freund et al | F24F 7/00 | + |
| 5,786,598A | July 1998 | Clark et al | B65B 55/08 | ++ |
| 5,808,402A | September 1998 | Seiler et al | H01J 61/00 | + |
| 5,814,135A | September 1998 | Weinberg | A61L 9/22 | ++ |
| 5,827,611A | October 1998 | Forbes | D02G 3/00 | x |
| 5,884,660A | March 1999 | Cathrein | B65B 39/002 | + |
| 5,887,807A | March 1999 | Beinecke | B02C 18/06 | + |
| RE 36,157E | March 1999 | Robbins et al | B32B 31/26 | + |
| 5,889,684A | March 1999 | David et al | G01F 23/70 | x |
| 5,891,399A | April 1999 | Owesen | A61L 9/20 | ++ |
| 5,904,896A | May 1999 | High | A61C 19/00 | +++ |
| 5,925,885A | July 1999 | Clark et al | B65B 55/08 | ++ |
| 5,961,000A | October 1999 | Sanfilippo | B65B 31/00 | x |
| 5,967,778A | October 1999 | Riitano | A61C 19/002 | ++ |
| 5,973,904A | October 1999 | Pui et al | B05B 5/053 | ++ |
| 5,974,347A | October 1999 | Nelson | B62D 5/04 | x |
| 5,993,738A | November 1999 | Goswani | A61L 9/18 | +++ |
| 6,014,890A | January 2000 | Breen | G01N 19/10 | + |
| 6,026,959A | February 2000 | Lowe | A61M 5/3205 | ++ |
| 6,042,637A | March 2000 | Weinberg | A61L 9/22 | ++ |
| 6,053,314A | April 2000 | Pittman | A61M 5/3205 | ++ |
| 6,054,324A | April 2000 | Sullivan et al | G01N 1/28 | +++ |
| 6,090,921A | July 2000 | Winge | A61K 35/14 | ++ |
| 6,099,522A | June 2000 | Knopp et al | A61N 5/02 | + |
| 6,142,303A | November 2000 | Dendy et al | B65D 69/00 | ++ |
| 6,149,717A | November 2000 | Satyapal et al | B03C 3/011 | +++ |
| 6,153,968A | November 2000 | Dombrowski et al | H01J 19/12 | ++ |
| 6,184,517B1 | February 2001 | Sawada et al | G01V 8/00 | ++ |
| 6,187,271B1 | February 2001 | Lee et al | A62B 7/08 | ++ |
| 6,242,753B1 | June 2001 | Sakurai | A61L 2/10 | ++ |
| 6,249,077B1 | June 2001 | Brown et al | H01J 17/28 | ++ |
| 6,258,577B1 | July 2001 | Goodrich, Jr et al | C12N 13/00 | ++ |
| 6,274,973B1 | August 2001 | Mochiduki et al | H01J 5/56 | ++ |
| 6,277,337B1 | August 2001 | Goodrich, Jr et al | B01J 19/08 | ++ |
| 6,288,780B1 | September 2001 | Fairley et al | G01N 21/00 | + |
| 6,305,820B1 | October 2001 | Poon | F21L 4/00 | x |
| 6,315,113B1 | November 2001 | Britton | A61M 5/3202 | +++ |
| 6,332,534B1 | December 2001 | Hammett | B65D 83/10 | + |
| 6,351,070B1 | February 2002 | Barry | H01J 7/46 | + |
| 6,419,749B1 | July 2002 | Rhoades | B05B 5/00 | + |
| 6,423,830B1 | July 2002 | Winge | A61K 35/14 | + |
| 6,433,343B1 | August 2002 | Cimino et al | A61L 2/10 | + |
| 6,460,328B1 | August 2002 | Hertzberg | F01N 3/00 | + |
| 6,405,798B1 | August 2002 | Barrett et al | F21B 44/00 | x |
| 6,468,428B1 | October 2002 | Nishii | B01D 53/88 | + |
| 6,471,136B1 | October 2002 | Chatterjee et al | G05D 23/00 | ++ |
| 6,514,721B2 | February 2003 | Spurrell | C12Q 1/24 | +++ |
| 6,534,770B2 | March 2003 | Miller et al | A618 6/00 | + |
| 6,535,838B2 | March 2003 | Abraham et al | G06F 11/30 | x |
| 6,566,659B1 | May 2003 | Clark et al | B65B 55/08 | +++ |
| 6,588,807B1 | July 2003 | Burke | F16L 37/100 | x |
| 6,626,606B1 | September 2003 | Johnson | E06B 11/00 | x |
| 6,637,587B2 | October 2003 | Britton | A61M 5/3278 | +++ |
| 6,656,424B1 | December 2003 | Deal | A61L 2/10 | +++ |
| 6,660,068B1 | December 2003 | Garner et al | B01D 39/00 | ++ |
| 6,701,772B2 | March 2004 | Kierchauf et al | B25J 19/02 | ++ |
| 6,759,664B2 | July 2004 | Thompson et al | G01N 21/06 | +++ |
| 6,788,404B2 | September 2004 | Lange | G01N 21/00 | + |
| 6,837,922B2 | January 2005 | Gorin | B01D 35/143 | + |
| 6,843,961B2 | January 2005 | Hlavinka et al | A61L 2/00 | + |
| 6,861,036B2 | March 2005 | Biswas et al | B01J 19/08 | + |
| 6,915,205B2 | July 2005 | Kim et al | G01C 21/26 | x |
| 6,941,193B2 | September 2005 | Frecska et al | G05B 15/02 | +++ |
| 7,068,361B2 | June 2006 | Cimino | G011 1/00 | + |
| 7,080,816B1 | July 2006 | Vaccaro | F16M 13/00 | x |
| 7,119,689B2 | October 2006 | Mallett | B07C 7/005 | ++ |
| 7,186,371B1 | March 2007 | Warling | A61L 2/00 | + |
| 7,187,111B1 | March 2007 | Johanning | H01J1/92 | x |
| 7,204,429B2 | April 2007 | Olney | F24F 11/77 | ++ |
| 7,217,936B2 | May 2007 | Ressler | A61L 2/10 | + |
| 7,244,294B2 | July 2007 | Kates | B01D 46/42 | + |
| 7,261,443B1 | August 2007 | Hayes, Jr | F21V 21/34 | x |
| 7,380,627B2 | June 2008 | Huang et al | B60R 27/00 | +++ |
| 7,401,469B2 | July 2008 | Joshi et al | F25B 49/00 | ++ |
| 7,423,367B2 | September 2008 | Lantis et al | H01J 19/12 | +++ |
| 7,427,167B2 | September 2008 | Holder et al | G02B 6/36 | x |
| 7,435,982B2 | October 2008 | Smith | A61N 5/06 | ++ |
| 7,452,561B2 | November 2008 | Newman | A23B 7/015 | + |
| 7,459,694B2 | December 2008 | Scheir et al | A61L 2/10 | +++ |
| 7,476,006B2 | January 2009 | Hinds | F21S 8/00 | x |
| 7,522,703B2 | April 2010 | Okuyama et al | G21K 5/10 | ++ |
| 7,674,440B2 | March 2010 | Martin | A61L 2/00 | ++ |
| 7,677,411B2 | March 2010 | Crowder | B67B 7/00 | + |
| 7,705,331B1 | April 2010 | Kirk et al | G21G 4/00 | + |
| 7,767,169B2 | July 2005 | Snyder et al | B01J 19/08 | ++ |
| 7,796,727B1 | September 2010 | Kaufman | G21K 5/00 | ++ |
| 7,829,867B2 | November 2009 | Hlavinka et al | A61L 2/08 | ++ |
| 7,897,104B2 | March 2011 | Kwon | A61L 2/00 | + |
| 7,989,786B2 | August 2011 | Smith et al | G01J 3/10 | ++ |
| 8,021,608B2 | September 2011 | Skrobot et al | A61L 2/00 | ++ |
| 8,029,608B1 | October 2011 | Breslin | B01D 49/00 | + |
| 8,242,695B2 | August 2012 | Sumitomo et al | H01J 17/20 | +++ |
| 8,295,690B2 | October 2012 | Brooke et al | A45D 20/40 | x |

REFERENCES CITED:
U.S. PATENT DOCUMENTS:

| Patent | Date | Inventor | Class | Rating |
|---|---|---|---|---|
| 8,298,482 B2 | October 2012 | Rees et al | A61L 9/015 | ++ |
| 8,309,943 B2 | November 2012 | Smith et al | H01J 63/08 | +++ |
| 8,436,152 B2 | May 2013 | Brinkman | C07K 1/30 | + |
| 8,474,304 B2 | July 2013 | Knopf | G01N 1/22 | + |
| 8,551,399 B2 | October 2013 | Shannon et al | A61L 2/20 | ++ |
| 8,613,297 B2 | December 2013 | Adams | B65B 1/04 | + |
| 8,653,245 B2 | February 2014 | Brinkman et al | C07K 1/14 | + |
| 8,658,067 B2 | February 2014 | Peno et al | D01D 5/18 | + |
| 8,702,829 B2 | April 2014 | Lise et al | B01D 46/10 | x |
| 8,828,315 B2 | September 2014 | Ryska et al | A23B 7/152 | ++ |
| 8,926,489 B2 | January 2015 | Brunson | B65D 81/00 | ++ |
| 8,962,802 B2 | February 2015 | Brinkman | C07K 1/14 | + |
| 9,072,803 B2 | July 2015 | Sakaki | A61L 2/18 | +++ |
| 9,144,831 B2 | September 2015 | Sappok et al | B08B 7/02 | + |
| 9,165,756 B2 | October 2015 | Stibich et al | H01J 61/025 | ++ |
| 9,185,877 B2 | November 2015 | Crabtree et al | A01K 1/0064 | + |
| 9,187,551 B2 | November 2015 | Dasseux | C07K 14/775 | x |
| 9,198,994 B2 | December 2015 | Suissa et al | A61L 9/12 | ++ |
| 9,201,428 B2 | December 2015 | Dietz et al | G05D 7/0688 | + |
| 9,308,492 B2 | April 2016 | Obee et al | B01D 53/32 | ++ |
| 9,310,091 B2 | April 2016 | Hoglund et al | F24F 11/0012 | + |
| 9,310,581 B2 | April 2016 | Faria | G02B 7/006 | + |
| 9,339,266 B2 | May 2016 | Alcouloumre | A61B 17/06114 | + |
| 9,364,575 B2 | June 2016 | Habbel | A61L 9/122 | ++ |
| 9,368,337 B2 | June 2016 | Antsiferov et al | H01J 61/025 | +++ |
| 9,392,726 B2 | July 2016 | Shelnutt et al | H05K 7/20145 | + |
| 9,399,186 B2 | July 2016 | Welke | B01D 46/444 | ++ |
| 9,423,143 B2 | August 2016 | Emmons et al | F24F 7/04 | + |
| 9,451,730 B2 | September 2016 | Gardner | H05K 7/20745 | + |
| 9,457,121 B1 | October 2016 | Davis | A61L 9/20 | ++ |
| 9,504,255 B2 | November 2016 | Cai | A61N 55/00 | +++ |
| 9,518,082 B2 | December 2016 | Allison et al | C07K 1/22 | +++ |
| 9,552,715 B2 | January 2017 | Breslin | G08B 21/18 | +++ |
| 9,587,195 B2 | March 2017 | Brewer | C10L 10/14 | + |
| 9,623,352 B2 | April 2017 | Kas et al | B01D 39/1607 | + |
| 9,638,432 B2 | May 2017 | Sinur et al | F24F 11/0009 | + |
| 9,662,161 B2 | May 2017 | Ganem et al | A61B 18/00 | ++ |
| 9,670,456 B2 | June 2017 | Mundt et al | C12N 5/0602 | ++ |
| 9,682,345 B2 | June 2017 | Gromala et al | B01D 53/82 | ++ |
| 9,688,950 B2 | June 2017 | Roulston | C12M 21/02 | ++ |
| 9,694,308 B2 | July 2017 | Michael et al | B01D 46/44 | + |
| 9,695,084 B2 | July 2017 | Spitler et al | C03C 17/3405 | + |
| 9,698,003 B2 | July 2017 | Stibich et al | H01J 61/025 | +++ |
| 9,700,072 B2 | July 2017 | Dobrinsky et al | A23L 3/28 | +++ |
| 9,707,047 B2 | July 2017 | Woodward | A61B 50/362 | +++ |
| 9,707,307 B2 | July 2017 | Shur et al | A61L 2/10 | +++ |
| 9,720,102 B1 | August 2017 | Page et al | G01T 1/2002 | ++ |
| 9,724,441 B2 | August 2017 | Shur et al | A61L 2/10 | ++ |
| 9,744,255 B2 | August 2017 | Stibich | A61L 2/24 | +++ |
| 9,744,491 B2 | August 2017 | Cordova | B01D 46/0023 | + |
| 9,744,495 B2 | August 2017 | Tu et al | B01D 47/06 | ++ |
| 9,751,038 B2 | September 2017 | Frankel et al | B01D 53/0407 | + |
| 9,757,735 B2 | September 2017 | Wang | B03C 3/361 | ++ |
| 9,759,438 B2 | September 2017 | Cur el al | F24F 3/1603 | + |
| 9,759,442 B2 | September 2017 | Dietz et al | F24F 11/0001 | + |
| 9,759,673 B2 | September 2017 | Rapoport | G01N 24/08 | ++ |
| 9,763,478 B2 | September 2017 | Cameron et al | A24F 47/008 | + |
| 9,764,266 B1 | September 2017 | Carter | B01D 46/0005 | + |
| 9,770,149 B2 | September 2017 | Son | A47L 9/0072 | + |
| 9,770,192 B2 | September 2017 | Fuisz et al | A61B 5/097 | + |
| 9,772,340 B1 | September 2017 | Yosi et al | G01N 35/00732 | + |
| 9,773,658 B2 | September 2017 | Stibich et al | H01J 61/40 | + |
| 9,775,924 B2 | October 2017 | Tanimoto et al | A61L 2/208 | +++ |
| 9,789,430 B2 | October 2017 | Jackson | B01D 46/0024 | + |
| 9,789,480 B2 | October 2017 | Funazuka et al | B01L 1/04 | ++ |
| 9,791,161 B2 | October 2017 | Fujishir et al | F24F 9/00 | + |
| 9,795,957 B2 | October 2017 | Holtz et al | B01L 1/04 | ++ |
| 9,797,609 B2 | October 2017 | Sekiguchi et al | F24F 3/1607 | ++ |
| 9,802,145 B2 | October 2017 | Yu et al | B01D 46/0039 | + |
| 9,802,355 B2 | October 2017 | Snyder | B29C 64/106 | ++ |
| D 802,725 S | November 2017 | Stoner, Jr et al | D23/355 | x |
| 9,808,754 B2 | November 2017 | Stoner, Jr et al | B01D 46/001 | ++ |
| 9,808,760 B2 | November 2017 | Gromala et al | B01D 53/82 | +++ |
| 9,808,808 B2 | November 2017 | Wen et al | B03C 3/08 | ++ |
| 9,821,260 B2 | November 2017 | Stoner, Jr et al | B01D 46/4254 | ++ |
| 9,827,728 B2 | November 2017 | Kay et al | B29D 99/0078 | + |
| 9,834,806 B2 | December 2017 | Noda et al | C12Q 1/008 | ++ |
| 9,839,868 B2 | December 2017 | Fritze | B01D 35/153 | + |
| 9,839,872 B2 | December 2017 | Spartz | B01D 53/1487 | + |
| 9,844,896 B2 | December 2017 | Adriansens | B29C 37/00 | + |
| 9,849,415 B2 | December 2017 | Patel | B01D 46/0023 | + |
| 9,851,289 B2 | December 2017 | Kinugasa | G01N 15/1434 | + |
| 9,855,522 B2 | January 2018 | Yu et al | B01D 46/0039 | + |
| 9,857,301 B1 | January 2018 | Nourbakhsh et al | G01N 21/4738 | ++ |
| 9,863,317 B2 | January 2018 | Santini et al | F02C 7/05 | + |
| 9,873,076 B2 | January 2018 | Dralle | B01D 46/023 | + |
| 9,880,097 B2 | January 2018 | Evenstad et al | G01N 21/53 | + |
| 9,895,462 B2 | February 2018 | Law et al | A61L 9/00 | + |
| 9,908,071 B2 | March 2018 | Scofield | B01D 46/0086 | ++ |
| 9,919,816 B2 | March 2018 | Tenegal | B65B 1/04 | +++ |
| 9,920,947 B2 | March 2018 | Breslin | F24F 11/0086 | +++ |
| RE 46,804 E | April 2018 | Zhang | B01D 53/0454 | +++ |
| 9,931,641 B2 | April 2018 | Chan et al | B03C 3/363 | ++ |
| 9,938,724 B2 | April 2018 | Walters | F04F 13/074 | x |
| 9,943,619 B2 | April 2018 | Toso | A61L 2/18 | +++ |
| 9,943,620 B2 | April 2018 | Bender et al | A61L 2/20 | ++ |
| 9,949,881 B2 | April 2018 | Self et al | A61G 13/108 | + |
| 9,956,515 B2 | May 2018 | Stinzendoerfer et al | B01D 46/0036 | + |
| 9,957,052 B2 | May 2018 | Fox et al | B64D 13/06 | ++ |
| 9,962,457 B2 | May 2018 | Faurie et al | A61L 9/20 | +++ |
| 9,962,642 B2 | May 2018 | Morison | B01D 46/02 | + |
| 9,974,880 B2 | May 2018 | Krosney | A61L 9/20 | +++ |
| 9,974,881 B2 | May 2018 | Kim et al | A61L 9/205 | +++ |
| 9,974,917 B2 | May 2018 | Bafile et al | A61M 16/08 | x |
| 9,980,748 B2 | May 2018 | Worrilow | A61B 17/42 | +++ |
| 9,981,056 B2 | May 2018 | Al-Zeer et al | A61L 9/205 | +++ |
| 9,981,532 B2 | May 2018 | Blackley | B60H 3/0035 | ++ |
| 9,982,247 B2 | May 2018 | Bataille et al | C12N 9/24 | ++ |
| 9,987,098 B2 | June 2018 | Robert et al | A61B 90/70 | + |
| 9,988,691 B2 | June 2018 | Sislian | C12Q 1/689 | ++ |
| 9,988,664 B2 | June 2018 | Ensor et al | C12Q 1/24 | ++ |
| 9,999,853 B2 | June 2018 | Knapke et al | B01D 53/82 | + |
| 10,006,847 B2 | June 2018 | Twigg | G01N 15/065 | + |
| 10,006,848 B2 | June 2018 | Woolard et al | G01N 15/082 | ++ |
| 10,006,850 B2 | June 2018 | Irie | G01N 15/1404 | + |
| 10,006,871 B2 | June 2018 | Kaufman | G01N 21/94 | ++ |
| 10,010,459 B2 | July 2018 | Sonntag et al | A61F 13/535 | + |
| 10,010,487 B2 | July 2018 | Py et al | A61J 11/0005 | + |
| 10,016,350 B2 | July 2018 | Pohlmann et al | A61K 8/40 | ++ |
| D 825,046 S | August 2018 | Eurich et al | D 23/355 | + |
| 10,039,327 B2 | August 2018 | Cameron | A24F 47/008 | + |
| 10,042,369 B2 | August 2018 | Blackley | G05D 7/0676 | ++ |
| 10,042,408 B2 | August 2018 | Cameron et al | G06F 1/266 | + |
| 10,046,261 B2 | August 2018 | Dietz | B01D 46/0023 | ++ |
| 10,046,323 B2 | August 2018 | Bos | B01L 3/50825 | + |
| 10,058,128 B2 | August 2018 | Cameron et al | A24F 47/008 | + |
| 10,060,893 B2 | August 2018 | Prusik et al | G01N 31/229 | + |
| D 828,529 S | September 2018 | Hu | D 23/364 | + |
| 10,066,847 B2 | September 2018 | Zhang et al | F24F 17/30 | ++ |
| 10,071,177 B1 | September 2018 | Kellogg, Jr | A61L 2/208 | +++ |
| 10,077,912 B2 | September 2018 | Hong | F24F 3/14 | x |
| 10,080,985 B2 | September 2018 | Nagy et al | B01D 39/28 | + |
| 10,085,608 B2 | October 2018 | Kim et al | A47L 11/4011 | + |
| 10,086,098 B2 | October 2018 | Johnson | A61L 2/18 | + |
| 10,086,963 B2 | October 2018 | Py et al | B65B 55/10 | ++ |
| 10,087,235 B2 | October 2018 | Warren et al | C07K 14/775 | +++ |
| 10,088,358 B1 | October 2018 | O'Driscoll et al | G01J 1/429 | + |
| 10,092,666 B2 | October 2018 | Quagliarella et al | A61L 2/16 | ++ |
| 10,092,672 B2 | October 2018 | Hingorani et al | A61L 9/20 | + |
| 10,092,870 B2 | October 2018 | Sweet et al | B01D 46/0005 | + |
| 10,101,258 B2 | October 2018 | Kaufman et al | G01N 15/082 | +++ |
| 10,104,867 B2 | October 2018 | Gabriel et al | A91K 1/03 | + |
| 10,111,337 B1 | October 2018 | Stumm et al | H05K 5/0091 | +++ |
| D 832,988 S | November 2018 | Stoner, Jr et al | D 23/355 | + |
| 10,118,013 B2 | November 2018 | Krietzman | A61M 21/02 | ++ |
| 10,124,081 B2 | November 2018 | Agafonov et al | A61L 2/10 | ++ |

REFERENCES CITED:
U.S. PATENT DOCUMENTS:

| | | | | |
|---|---|---|---|---|
| 10,132,679B2 | November 2018 | Emadi et al | G01J 1/429 | + |
| 10,137,216B2 | November 2018 | Goswami et al | A61L 9/205 | + |
| 10,137,392B2 | November 2018 | Snyder | B01D 39/18 | + |
| 10,139,118B2 | November 2018 | Law et al | F24F 6/00 | + |

RATING OF PRIOR ART PATENT VALUE FOR THIS PATENT IN APPLICATION---
+++ = Relevant
++ = Related
+ = Of Interest
x = Of No Interest
------Shown Here

U.S. PATENTS IN APPLICATION

| | | | | |
|---|---|---|---|---|
| 2002/0012252A1 | January 2002 | Carter et at | F21V 8/00 | + |
| 2002/0021508A1 | February 2002 | Ishihara | G02B 17/00 | + |
| 2002/0119205A1 | August 2002 | Hassan | A61K 33/18 | x |
| 2002/0134234A1 | September 2002 | Kalbassi | B01D 53/0462 | x |
| 2002/0145063A1 | October 2002 | Mosensen et at | B02C 19/12 | x |
| 2002/0155229A1 | October 2002 | Rhoades | B05D 3/06 | ++ |
| 2003/0020403A1 | January 2003 | Okubo et al | H01J 61/04 | ++ |
| 2003/0089647A1 | May 2003 | Tsuihiji | B01D 29/15 | ++ |
| 2003/0165398A1 | September 2003 | Waldo et al | A61L 2/00 | ++ |
| 2003/0168389A1 | September 2003 | Astle et at | B01D 35/143 | + |
| 2003/0168982A1 | September 2003 | Kim | H01J 17/16 | ++ |
| 2003/0170152A1 | September 2003 | Kobayashi et at | A61L 2/00 | ++ |
| 2003/0231496A1 | December 2003 | Sato et al | F21V 13/04 | ++ |
| 2004/0003511Al | January 2004 | Silver | F26B 19/00 | x |
| 2004/0026512A1 | February 2004 | Otsubo | G06K 7/10 | + |
| 2004/0076568A1 | April 2004 | Yan | B01D 53/02 | ++ |
| 2004/0191125A1 | September 2004 | Kellogg | G01N 9/30 | + |
| 2004/0244138A1 | December 2004 | Taylor | A47L 9/2805 | x |
| 2004/0264512A1 | December 2004 | Hartlove et at | H01S 3/30 | +++ |
| 2004/1755390A1 | September 2004 | Scheir | A61L 3/28 | x |
| 2005/0072758A1 | April 2005 | Jackson et al | H23H 1/00 | x |
| 2005/0165499A1 | July 2005 | Stein | A238 7/152 | x |
| 2005/0167618A1 | August 2005 | Hoshino et al | G01J 1/00 | +++ |
| 2005/0178977A1 | August 2005 | Koenck | A23B 4/015 | x |
| 2005/0193585A1 | September 2005 | Silver | F26B 9/06 | x |
| 2005/0217282A1 | October 2005 | Strohm | A23B 7/152 | x |
| 2005/0218773A1 | October 2005 | Ono et al | H01J 1/30 | + |
| 2005/0269254A1 | December 2005 | Roitman | H01D 36/00 | + |
| 2005/0269521A1 | December 2005 | Zagrobelay | A61L 2/10 | ++ |
| 2005/0275547A1 | December 2005 | Kates | G08B 19/00 | x |
| 2006/0008378A1 | January 2006 | Imai et at | A61L 2/20 | +++ |
| 2006/0032213A1 | February 2006 | Woll | F01N 3/0871 | x |
| 2006/0044548A1 | March 2006 | Lee | G01F 1/00 | + |
| 2006/0053772A1 | March 2006 | Dou | F01N 3/0814 | x |
| 2006/0102731A1 | May 2006 | Mueller et al | F23N 5/20 | x |
| 2006/0110348A1 | May 2006 | Ohlhausen et at | A61K 8/00 | ++ |
| 2006/0144224A1 | July 2006 | Howard | B01D 53/02 | x |
| 2006/0150754A1 | July 2006 | Burtscher | B03C 3/08 | x |
| 2006/0249384A1 | November 2006 | Kim | G01N 27/127 | + |
| 2006/0257877A1 | November 2006 | Anderle et al | C12Q 1/68 | ++ |
| 2006/0202369A1 | September 2006 | Foreman | B29D 11/00173 | + |
| 2006/0266132A1 | November 2006 | Cheng | C01N 15/0266 | +++ |
| 2006/0284109A1 | December 2006 | Scheir | A61L 9/20 | +++ |
| 2007/0054803A1 | March 2007 | Myyairi | B01D 46/2429 | x |
| 2007/0104841A1 | May 2007 | Min | A23L 3/005 | x |
| 2007/0111150A1 | May 2007 | Hijikata | C09C 1/50 | x |
| 2007/0122257A1 | May 2007 | Bauer | B65D 88/30 | x |
| 2007/0196235A1 | August 2007 | Shur | A23L 3/28 | ++ |
| 2007/0205382A1 | September 2007 | Gaska | A61L 2/23 | +++ |
| 2007/0228300A1 | October 2007 | Smith | B82Y 10/00 | ++ |
| 2007/0231204A1 | October 2007 | Hyde | A61L 2/07 | ++ |
| 2007/0248487A1 | October 2007 | Kay | C02F 1/325 | +++ |
| 2007/0253860A1 | November 2007 | Schroder | A61L 9/015 | +++ |
| 2007/0277592A1 | December 2007 | Johansson et al | G01N 15/08 | ++ |
| 2008/0006636A1 | January 2008 | Wild | B65D 77/061 | x |
| 2008/0053195A1 | March 2008 | Matter | C09C 1/50 | x |
| 2008/0056933A1 | March 2008 | Moore | A47L 11/30 | ++ |
| 2008/0078466A1 | April 2008 | Wang | B65D 81/2038 | x |
| 2008/0105319A1 | May 2008 | Aniban, Jr | A01M 21/043 | x |
| 2008/0112845A1 | May 2008 | Dunn | A61L 9/205 | ++ |

U.S. PATENTS IN APPLICATION

| | | | | |
|---|---|---|---|---|
| 2008/0163610A1 | July 2008 | Baird | F01N 3/0842 | x |
| 2008/0199354A1 | August 2008 | Gordon | A61L 2/10 | ++ |
| 2008/0210085A1 | September 2008 | Morf | B01D 53/12 | + |
| 2008/0213129A1 | September 2008 | van der Pol | A61L 2/10 | ++ |
| 2008/0260601A1 | October 2008 | Lyon | A61L 2/10 | ++ |
| 2008/0305257A1 | December 2008 | Tenegal | B01D 47/16 | ++ |
| 2009/0032740A1 | February 2009 | Smith et al | G01J 1/00 | ++ |
| 2009/0129974A1 | May 2009 | McEllen | A61L 9/205 | ++ |
| 2009/0151567A1 | June 2009 | Krigmont | B03C 3/025 | + |
| 2009/0185960A1 | July 2009 | Busujima | A61L 2/208 | +++ |
| 2009/0191100A1 | July 2009 | Deal | A61L 2/10 | +++ |
| 2009/0194189A1 | August 2009 | Bordere | B65B 1/28 | + |
| 2009/0242674A1 | October 2009 | Lee et al | B02C 21/00 | x |
| 2009/0260518A1 | October 2009 | Wright | B01D 53/0462 | x |
| 2009/0280035A1 | November 2009 | Koudymov | A23L 3/28 | ++ |
| 2009/0285362A1 | November 2009 | Bimbach | A23L 3/263 | ++ |
| 2009/0314164A1 | December 2009 | Yamashita | F24F 3/1603 | ++ |
| 2009/0314308A1 | December 2009 | Kim | A61L 2/0047 | ++ |
| 2010/0001184A1 | January 2010 | Chen | G01N 15/0266 | ++ |
| 2010/0068897A1 | March 2010 | Liu | H01L 21/3105 | + |
| 2010/0018853A1 | January 2010 | Robinson | B01J 2/02 | x |
| 2010/0155626A1 | June 2010 | Dougherty | G21F 5/06 | x |
| 2010/0071554A1 | March 2010 | Pfeffer | B01D 39/06 | ++ |
| 2010/0078574A1 | April 2010 | Cooper | B01J 19/123 | +++ |
| 2010/0101432A1 | April 2010 | Biotti | A23L 3/3418 | x |
| 2010/0242299A1 | September 2010 | Siegel | B41F 23/0409 | + |
| 2010/0264820A1 | October 2010 | Sumitomo et al | H01J 61/20 | +++ |
| 2010/0284903A1 | November 2010 | Harityununyan | B01D 53/32 | ++ |
| 2010/0296971A1 | November 2010 | Gaska | A61L 2/10 | ++ |
| 2010/0298134A1 | November 2010 | De Leede | B01D 53/02 | x |
| 2011/0004339A1 | January 2011 | Ozick | A47L 5/30 | x |
| 2011/0005832A1 | January 2011 | McDonald | F21B 11/065 | x |
| 2011/0048541A1 | March 2011 | Wehrli | B28C 7/0007 | x |
| 2011/0054574A1 | March 2011 | Felix | A61L 2/0047 | ++ |
| 2011/0073774A1 | March 2011 | Taylor | A61L 2/10 | + |
| 2011/0087008A1 | April 2011 | Brinkman | C07K 14/775 | + |
| 2011/0097896A1 | April 2011 | Daamen et al | H01L 21/68 | x |
| 2011/0147617A1 | June 2011 | Shur | G01N 21/64 | +++ |
| 2011/0178029AI | July 2011 | Knudsen | C07K 14/775 | x |
| 2011/0182066A1 | July 2011 | Webb | F21V 21/22 | x |
| 2011/0189460A1 | August 2011 | Chavdar | F16D 69/026 | x |
| 2011/0206554A1 | August 2011 | Anderle | A23L 3/26 | ++ |
| 2011/0215261A1 | August 2011 | Lyslo | A61L 2/10 | ++ |
| 2011/0247396A1 | October 2011 | Zhang | G01N 53/0029 | ++ |
| 2011/0268606A1 | November 2011 | Glazer et al | A61L 2/20 | x |
| 2011/0271873A1 | November 2011 | Ohlhausen et al | C09D 5/00 | x |
| 2011/0297241A1 | December 2011 | Biotti | A23L 3/3418 | x |
| 2012/20037232A1 | February 2012 | Shen | B01F 11/0266 | + |
| 2012/0045363A1 | February 2012 | Gil | A61L 2/10 | + |
| 2012/0056102A1 | March 2012 | Stanley | G01J 1/0271 | +++ |
| 2012/0085116A1 | April 2012 | Maeng | F25D 17/042 | + |
| 2012/0093688A1 | April 2012 | Harmon | A61L 2/10 | ++ |
| 2012/0119108A1 | May 2012 | Goldshtein | A61L 9/20 | +++ |
| 2012/0178877A1 | July 2012 | Rathje | B82Y 30/00 | + |
| 2012/0241601A1 | September 2012 | Kaufman | G01N 21/45 | ++ |
| 2012/0301360A1 | November 2012 | Meinhold | B01J 20/28047 | ++ |
| 2012/0305787A1 | December 2012 | Henson | A61L 2/10 | ++ |
| 2012/0313532A1 | December 2012 | Stibich | A61L 2/10 | ++ |
| 2012/0315186A1 | December 2012 | Davis | F21V 11/183 | ++ |
| 2012/0319851A1 | December 2012 | Hoglund | G08B 21/18 | +++ |
| 2013/0061659A1 | March 2013 | Ajay | G01N 1/2205 | + |
| 2013/0094211A1 | April 2013 | Drake | F21V 11/183 | + |
| 2013/0174643A1 | July 2013 | Wang | G01N 15/0272 | +++ |
| 2013/0186269A1 | July 2013 | Cheng | B01D 53/228 | +++ |
| 2013/0313196A1 | November 2013 | Hufen | C02F 1/441 | ++ |
| 2013/0334175A1 | December 2013 | Jackson et al | A61M 5/32 | x |
| 2013/0337121A1 | December 2013 | Sugano | A23B 4/015 | + |
| 2014/0060094A1 | March 2014 | Shur | A61L 2/10 | ++ |
| 2014/0060095A1 | March 2014 | Shur | A61L 2/10 | ++ |
| 2014/0060104A1 | March 2014 | Shur | A61L 2/10 | ++ |
| 2014/0166624A1 | June 2014 | Butler | A61M 5/32 | x |
| 2014/0174154A1 | June 2014 | Marra | G01N 1/2273 | + |
| 2014/0227861A1 | August 2014 | Wu | H01J 37/3211 | + |
| 2014/0234165A1 | August 2014 | Glazer et al | B09B 3/00 | x |

-continued

U.S. PATENTS IN APPLICATION

| | | | | |
|---|---|---|---|---|
| 2014/0264070A1 | September 2014 | Bettles | A6IL 2/10 | +++ |
| 2014/0291552A1 | October 2014 | Schumacher | A47L 25/04 | ++ |
| 2015/0097048A1 | April 2015 | Linnell | B05B 7/0483 | ++ |
| 2016/0038624A1 | February 2016 | Krosney | B01D 53/007 | +++ |

FOREIGN PATENT DOCUMENTS:

| | | |
|---|---|---|
| CA | 2569130 | June 2008 |
| CN | 87203475 | August 1988 |
| CN | 2488020 Y | April 2002 |
| CN | 101171938 A | May 2008 |
| CN | 101322000 A | December 2008 |
| CN | 102564003 A | July 2012 |
| DE | 2356272 A | May 1975 |
| EP | 1038536 | June 2005 |
| EP | 2174670 | April 2010 |
| EP | 2314802 | April 2011 |
| GB | 2452341 | March 2009 |
| JP | 07008541 A | January 1995 |
| JP | H08196606 | August 1996 |
| JP | 2002204653 | July 2002 |
| JP | 2003-262369 | September 2003 |
| JP | 2005-4380411 | November 2005 |
| JP | 2009-5163882 | December 2009 |
| JP | 2010-276737 | December 2010 |
| KR | 2006-0102300 | September 2006 |
| KR | 1020090074966 | July 2009 |
| KR | 1020110057773 | June 2011 |
| KR | 1020120011458 | February 2012 |
| WO | 0074731 | December 2000 |
| WO | 01/06905 | February 2001 |
| WO | 2005/082426 | September 2005 |
| WO | 2007/076359 | July 2007 |
| WO | 2010/134838 A1 | November 2010 |
| WO | 2013/096243 A1 | June 2013 |
| WO | 2014/022717 | June 2014 |
| WO | 2014/100493 | June 2014 |

OTHER PUBLICATIONS

Angrist, Stanley W. Direct Energy Conversion. Allyn & Bacon, Inc., Boston, Third Edition, 1976, 518 pages.

Bennett, H., FAIC. The Chemical Formulary. New York, Publishing Company, Inc., 1977, 399 pages.

Brady, James E. & John R. Hoium. Fundamentals of Chemistry. New York, John Wiley & Sons, Third Edition, 1988, 1055 pages text, 107 pages in Appendices.

Chen, Phillip S. Chemistry: Inorganic, Organic, & Biological. Barnes & Noble Books, A Division of Harper & Row Publishers, New York, 1968, 263 pages.

Day, David. The Environmental Wars. New York, St. Martins Press, 1989.

Ganghi, Om P. Microwave Engineering & Applications. Pergamon Press: New York, 1981, 543 pages.

Howes, M. J. & D. V. Morgan, editors. Microwave Devices: Device Circuit Interactions. John Wiley & Sons: New York, 1976, 1978, 402 pages.

Lange, Norbert Adolph, PhD, Editor, & assisted by George M. Forker, B. S, [Chem. Eng.]. Handbook of Chemistry. A reference volume for all requiring ready access to Chemical & physical data used in laboratory work & manufacturing. Sandusky, Ohio, Handbook Publishers, Inc., Eighth Edition, 1952, 1998 pages.

Smith, Arthur W., & M. L. Wiedenbeck. Electrical Measurements. McGraw-Hill Book Company, Inc., Fifth Edition, 1959, 307 pages.

Strum, R. D. & J. R. Ward. Electric Circuits & Networks. Quantum Publishers: New York, 1973, 437 pages.

Taylor, Nick. LASER: The Inventor, The Nobel Laureate, The Thirty-Year Patent War, Simon & Schuster: New York, 2000, 304 pages.

FIELD OF SEARCH

While the standard U.S. Classification System of just over 200 years has been modernized to meet the now accepted International Standards and has been passed into law in the America Invents Act [AIA] and now in full use with its new regulations and procedures. Thus, all entries herein are cited as AIA standards in this Classification Reference for all U. S. Patents in Application.

The Sections herein are:

Section A: Human Necessities;

Section B: Performing Operations; Transporting;

Section H: Electricity

The dominant and most numerous citations are in Section A under the A61 designations as "Medical or Veterinary Science; Hygiene". This is seen especially in A61L that performs "sterilizing, disinfection, or deodorizing" of items from the aftermath of surgery. Then, in A61N, there is covered electrotherapy and then the radiation therapy that obliterates genus from surgery, wounds, and skin, into the open air, plus any devices used.

The second most cited section is Section B under B01 designations as shown "Physics or Chemical Processes or Appearances in General" wherein that includes BO ID, as the sub-class of 'Separation', defined as "separating solids from solids [or fluids] by wet methods, and by other dry methods including electrical, electrostatic, magnetic, high voltage, ventilation, or filters."

The third most cited section is Section H under H01J sub-class would be designations such as "Electric Discharge Tubes or Electric Discharge Lamps" increasing to covered items such as switches of all various types, & pulsed lights with other electromagnetic devices such as X-Rays & Other Radiation, gas vapors, high intensity light sources and light generation, including ultraviolet and other types.

In the research and development necessary to formulate and achieve this patent to clean up and clear out all infectious material that seems long residing in a hospital. These infectious germs are somewhat dormant, and out of sight, or out of reach, and they avoid any direct cleaning on the top surfaces in the patients' room as they live and colonize under chairs, couches, tables, beds, plus behind curtains, doors, mirrors and everywhere in the bathrooms. From time to time these germs come out of hiding to cross infect a patient with another disease while there die. Is such a problem a natural event in modern hospitals? Are "wrongful deaths" claimed in cases from cross infections? It does seem surprising that in more than 100 years of public hospitals no-one has attempted to resolve this dilemma with any satisfaction.

To research and develop all aspects as involved in such a situation and to sort through the many related prior art patents [more than 12,000 issued] I have chosen 7 categories that require investigation to be resolved as listed to follow in this Field of Search. The range of activities includes effective means to destroy or neutralize all pathogens, microbes, viruses, bacteria and fungi as such that all live out of sight in the hospitals. These issues will be found in every forced air ventilation system buildings with sealed shut windows. Most modern commercial office buildings as well as most government buildings everywhere now have sealed windows that do not open to ventilate. While the modem HEPA Air System is well balanced in its Air Delivery as the air moves throughout the building, and it can maintain its air even quite a far distance away from its location. The existing HEPA System uses forced air to reach out everywhere in its buildings efficiently, but it will not stop 0.3 micron particulates which carry almost all of the infectious germs right through the HEPA filters everywhere in the building to offer possible infections to every patient, all of the staff, nurses, doctors, interns, medical students, emergency room personnel, cafeteria workers, delivery people, and everyone in the public areas. They all get 'Dirty' air in the dirty hospital.

As the number of patents to review is extensive, and somewhat divided as to their relevance to this patent in application, the use of the Categories previously shown will be helpful, as will the below chart that includes a best means to differentiate relevance and value as your procedure through this patent.

The Field of Invention covers a wide range of issues with selected few having the most new ways to address and solve such issues. Strong relevant prior art shows avenues that attempt to resolve, and to follow is a chart with all relevance and values to be marked as to their importance.

RELEVANCE & VALUES to this Application

+++=RELEVANT; meaning that the cited patent has several features and components that are relevant in the prior art.

++=RELATED Values, meaning that this patent in application has a feature or component that can be construed as related in the prior art.

+=OF INTEREST only, wherein a feature may be noted to be similar, but not the same to this patent.

x=OF NO INTEREST or value as seen here.

However, the hospitals have the virulent, infectious germs over the years that abound in the patient rooms, corridors, clinics, and doctors' treatment rooms, and this patent will eliminate these germs as they move around or become airborne and pass into the inlet of the HEPA Ventilating System.

THE 7 CATEGORIES ARE AS FOLLOWS:

I. Acid Baths as Virulent Killers;

II. Ultraviolet Radiation;

III. Laser Radiation & Gases;

IV. Filters;

V. Sterilizing & Purification;

Air & Fluids, High Intensity Light & Pulsed Lights

VI. Sensors:

VII. Electric, Electrodes, Electrostatic, Magnetic, also Heat, Infa-Red, & Misc. Items.

BACKGROUND OF THE INVENTION

There are quite a few prior art patents herein referenced that do seek to control, modify, purify, and improve air in a building environment, and some are quite creative and achieve good results but in a small and limited manner. With this patent the goal is to clear and clean not only the patients' rooms, but the entire hospital will benefit as the existing HEPA Filter System would receive sterile and clean intake air from all patients' rooms, clinics, doctors' offices, waiting rooms, and everywhere possible in the hospital. Soon, the goal can be 'The Number One Cleanest Hospital in the Area' wherein the particulate count gets very, very low.

Today, the hospitals announce that they are Number One in their State with the most Doctors, Consulting Doctors, Nurses, Paramedics, Emergency Facilities, Labs, Operating Rooms, Patient Beds, High Tech Diagnostic Machines, Parking Lots for Everyone, perhaps Valet Parking & Parking Garages. All of the Real-Time Convenience Anyone Would Want! So, do you want a dirty hospital that has lots of parking, and expensive machines [that the tax-payer pays for], consulting Doctors, Fancy Rooms, or a Hospital that is safe and clean? Would you want a Number One Rated Clean Hospital, or a Number 2 Dirty and Infectious Hospital? Nothing is ever mentioned about Cross-Infections or Highest Death Rate of a truly Dirty Hospital. Is there any interest in a Clean Hospital without Cross-Infections?

Where can you go to get Pneumonia? Dengue Fever? "Mercer" [MRSA aka Methicillin Resistant *Staphylococcus Aureus*]? Flu? You would have to go to a Hospital. Go to Visit a Friend, or a Patient, or just stop by to inquire at a Clinic, to get sick! You can't get such germs in a food store, auto dealer, or a restaurant, or 7-11, or out in the public, or out in the open air, the germs are not there, or just too few to get you sick. You go to the Hospital because that's where the germs are. [Thanks, Willie Sutton]

The modem hospitals are dirty, and spread diseases everywhere with the help of HEPA [High Energy Particulate Absorber). The HEPA System itself is not at fault, even though this forced air ventilation system was developed in the time of the Second World War. Today the HEPA still does its job moving the air around in a building, but mostly now the windows are closed and do not open, especially in large cities where there are risks in opening a window on the 61" floor. Another factor is the inside air is not ever changed, air can be added to when the pressure in the building drops, then more air is needed to continue the proper ventilation. Some of the air inside a building can be years old, 10 or 20 years old and still full of germs. The standard HEPA System also cannot maintain its velocity and speed around inside the building to reach far distances when it is too restrictive of its flow path with restrictive filtering. Thus, the standard system cannot detain or absorb the smallest of microbes [0.3 microns or less] that cannot be seen by the eye, and that's where the germs are. They pass right through the HEPA System without interruption. But, the important question is where do these infectious invisible germs come from?

HEPA gets its diseases from the patients. HEPA gets them from the hallways and corridors, the nurses' stations, the clinics, waiting rooms, lobby, emergency treatment rooms, examination rooms, just about everywhere in the hospital. The infectious material floats around and moves about everywhere that has ventilation by the HEPA System. You need to breathe clean air almost 20,000 times a day, and so, HEPA will find You. If you are a patient this infectious material from everywhere will find You also. This is one way that hospitals give to everyone, including You, exposure to an infectious disease FREE of charge, every hour of every day. There has to be some way that the ventilating system can get those diseases. They get them from the patients. They get them from the clinics, doctors' waiting rooms, and treatment rooms, doctors' offices, emergency stations, because that's where the diseases are.

Usually, you will be found in those 'open to inspect' hospital gowns that are required to wear items while a patient. You might be covered in bandages or awaiting surgery, but you will have 'new friends' that you cannot see because they are too small. In your room, the long-awaiting infectious germs can move in with you to add to your troubles, or just feed on you as only they can. Your new friends don't stay with the healthy people that visit, or people that move around fast like nurses or doctors. They will stay with someone bedridden and unable to move with tubes in their arms. This is where the term "nosocomios" came from, meaning a 'cross-infection' that can attack and infect the bedridden patient with another disease while they are sleeping or drowsy, lying down, bedridden and cannot move, taking pills, and just can't get up, then they are perfect to infect. Doctors, Nurses, Visitors, Healthy People are hard to catch, but not The Bedridden. How can a clean smelling and visually well prepared room cause you any trouble? You went into a hospital to get well, not to get sick with another illness or infection.

Unfortunately this issue is all too familiar and commonplace today with tens of thousands of hospital patients becoming newly infected, and in some cases dying from this type of cross-infectious disease that is hiding in their room. Cross-infection, often called 'nosocomio' as a definition [Source: Cassell's Spanish Dictionary, page 583] is quite extensive and quite serious in modern hospitals that can kill and disable patients.

The hospitals are very dirty and dangerous to be in as a patient, as a receptionist. As a nurse, as staff that work inside, as a lab worker, or to work in food service or cleaning. Thousands upon thousands of microbes, pathogens, viruses, and bacteria, plus mold, yeasts, spores, dust motes, all float through the AIR every hour, every day. The particulate count in a hallway could exceed 80,000 per cubic foot, in a clinic reception area could exceed 100.000 per cubic foot, in the cafeteria could exceed 200,000 per cubic foot, every day. A hospital uses the same air in its building all year long, as it COSTS too much to cool or heat outside fresh air to come inside, so they use the same air all the time, day after day, year after year. These invisible and unseen infectious particulates kill more patients and staff each year across the country than cars. The patient goes into a hospital with one disease trying to be treated and cured, but can die from a new disease already there in the hospital.

The news media tells the public about the number of csr related deaths and about wartime deaths each year, but nothing is said about the number of patients and staff in a hospital that sicken and die each year from dirty air in the hospital carrying diseases. These invisible and unseen infectious air particulates kill more patients and staff than the entire Viet Nam War [it was c. 58,000 deaths]. In recent years deaths from car accidents has been less than 40,000 killed. Also, in recent years the estimate from "blood infections" is more than 99,000 deaths per year, and with a conservative estimate by U. S. Department of Labor at 250,000 deaths per year. In one recent journal issue, a researched total listed 440,000 deaths per year, and another broader listing from The Center for Disease Control [CDC] in Atlanta listed hospital deaths at 721,000 [for all types of hospital deaths]. There is no directed accounting for infected nurses, emergency station workers, or paramedics who breathe in infections in the air, or receive needle sticks or blood borne infections while working. Many just sicken over time, and just retire to go home to live out their lives as best they can, and die unnoticed and forgotten years later.

An excellent article by Robert Lee Hotz reviewing where the germs hide in a hospital room was printed in The Wall Street Journal on Apr. 28, 2015, wherein the article was entitled: "Researchers Map Where Hospital Pathogens are Lurking". In this article the sub title was "Bacteria by design", wherein he describes, 'Researchers are learning building materials, ventilation, humidity, and other interior design features affect the kinds of bacteria people encounter in hospitals.' There is shown a profile of a typical patient room, based on recent studies microbial DNA.

Air Conditioning Vents: Air from mechanically ventilated rooms tends to be dominated by a few closely linked bacteria related to known human pathogens and human associated bacteria related to known human pathogens and human associated.

Windows: Hospital Rooms when ventilated with open windows have greater bacterial diversity, with more plant & soil associated bacteria.

Chair: Microbes on chair seats are dominated by human bacteria from the gastro-intestinal tract, urogenital tract & skin.

Upholstery: Drug resistant staph [*staphylococcus*] germs can live up to a week on some common furniture fabrics. E-coli [*Escherichia coli*] can last 96 hours on some coverings.

Tray table: Strep [*Streptococcus*], which cause an estimated 700 million infections world-wide every year, can survive for months on a dry surface.

Patient bed: Within hours of a new patient's arrival, the new occupants personal collection of microbes spread throughout the room helping make the microbiome of each hospital room unique.

Showerhead: Moisture-loving bacteria living in showerheads include potential pathogens that are significantly different from microbes found elsewhere in the patient rooms.

Doorway: People come in & out of a patient's room about 100 times a day, shedding about 37 million bacteria every hour into the surrounding air or onto surfaces touched.

Counter tops: Depending on the material involved some surfaces can have thousands of different types of bacteria while others have only a few hundred.

Mobile phone: On the average, people touch their cell phones 150 times a day, seeding them with thousands of bacterial types.

His article in The Wall Street Journal from 2015 has taken you on an important tour of how many bacterial types exist in a hospital environment, and where and how myriads of bacteria survive, and how many cannot be reached to be cleaned. What is not addressed is that millions, even billions and trillions, are out of sight and not on the surface of counters and furniture in a patient's room. 'Out of Sight, Out of Mind' is an old saying, and since you cannot see the germs anywhere in the open air, you will never know just how many there are. Under the chair, under the couch, under the bed, under the chest of drawers, under the bedside serving tray, underneath and out of sight, out of mind is where they are. Also, you cannot reach them anyway, how can you clean under tables and chests, on the wall behind curtains or blinds, in the tubes that bring in the 'fresh' forced ventilation air for you to breathe. You cannot and you never will be able to clean off the germs that live in your room. And, if you are a patient, you are too sick to do it anyway. So, who is the easiest target? The swift, ever moving nurses, or doctors, or cleaning staff, who are somewhat used to these germs; or the bedridden patient lying immobilized in the bed?

In the article by Robert Lee Hotz in The Wall Street Journal takes you on an important tour, but out of sight, there are crevices and vast areas unreachable underneath everything that are forever festering with colonies of bacteria, fungus, mold, spores, motes, infectious diseases and these lush colonies of small pathogens and particulates can dislodge and float away from time to time into the open air in a building by the ventilating means provided by HEPA. These small invisible and unseen creatures live and grow and fester in patient's rooms and throughout the hospital and traditional cleaning just won't cut it. Ineffective cleaning is irresponsible and truly dangerous to Everyone who works in any part of this building, especially since the small air is re-circulated for many, many years [perhaps 20 to 30 years]—it is the same air over and over again. It circulates the same infectious invisible creatures until they find a new home, a place to live and grow—perhaps, YOU.

Hospitals abound in dangerous and irresponsible 'Dry Boxes' wherein infectious syringe needles and hazardous medical sharps are just thrown into a dry box to fester and outgas infected particulates out into the open air for HEPA to pick up and move around everywhere, How can a hospital clinic or corridor have 100,000 particulates per cubic foot in the ambient air. Does anywhere else have such a high count? Would Office Buildings, or Schools, or Government Buildings have such a high count of infectious materials? Do Homes have such a high count? Most of the particulates will be benign or acceptable without difficulty like plain dirt or dust you face every day without getting infected, and less dangerous microbes that are too scattered to be effective, and others likely that your system is already used to or able to control. While you wade through the myriads of pathogens thick and deep in the hallways and they clutter up the air, you likely are normally protected from any danger.

But, in every closed air system there is danger, especially so in hospitals, there is infectious material that can lead to your discomfort and sickness. While these particulates and pathogens are somewhat rare, the question is, 'Where do they come from'? Where can you find the infected material? Does infection come from Department Stores, from the Mall, or any other place besides the Hospital? Many thousands of patients who go to the hospital to be treated and saved get new disabilities or diseases, perhaps, death, from cross-infection found in the hospital.

In this invention in application, there is a novel, new, and non-obvious way to curb infections in a hospital or in clinics, emergency and rescue work, patient wards, in short, everywhere that injections and surgery are performed. Over time this invention will destroy every hidden infectious germ, bug, creature, or whatever that hides in a hospital; and the building will be clean and free of airborne floating invisible and unseen. This issue will soon become chaos and disaster for all hospitals and an evident issue in every building with forced air ventilation systems, even where you work. Not only the risks from germs, bugs, and creatures, but from 'super bugs'.

In my recent U.S. Pat. No. [9,707,047] entitled: "Chemical Gel to Dissolve Metal and Hazardous Medical Sharps" the extent of an allowed activity of a chemical gel in a claim [claim 2] reads: "The medical sharps acidic gel disinfectant and dissolving composition renders harmless infectious material or diseases selected from the group consisting of microbes, viruses, pathogens, and bacteria". A further claim [claim 5] indicates the efficacy of a gel in its activity as it reads: "A medical sharps acidic gel disinfecting and dissolvent blunts and corrodes metal medical sharps upon contact with said gel composition". What will happen over time is every infectious germ will move, expand, or relocate to become airborne and then available to be drawn into the closed air system to spread out all over the buildings.

In a recent 'U.S. News & World Report' that surveys all U.S. Children's Hospitals [189] for a national ranking [2018-19], wherein they are evaluated for exceptional care in six specialties in medical procedures. Other factors cited included: [a] Patient outcomes; [b] Availability of specialized care and advanced technologies; [c] Support services for patients and families; & [d) Commitment to best practices, including measures to prevent infections; [e] A national survey of pediatric specialists. Then it summarizes in a statement from UVA: "The commitment of our multidisciplinary team to constantly seek ways to improve care for our patients and their families is reflected in these honors from U.S. News." Said Ms. Pamela M. Sutton-Wallace, chief executive officer of UVA [University of Virginia] Medical Center and its Children's Hospital for their hard work." I wonder if the CEO of UVA Children's Hospital really means what she said about protecting the children from infection? In this invention in application these small invisible creatures can be totally eliminated as a virulent source of infection as it is borne through the air. Consider the positive effect that this invention can disinfect and dispose safely of ALL infectious pathogens, microbes, viruses, and bacteria that pass through the air. No infectious material, including all dangerous small invisible creatures, can survive as they pass though the air in the patient's room, and so their disposal becomes NON-HAZARDOUS Waste for normal disposal as common trash in a routine manner.

In the etiology of hospital issues regarding the management of infection from 'nosocomio' [previously described], Roberta Carson published an article in an effort to improve patient involvement with diseases, "Reduce Your Risk of Exposure to Superbugs in Hospitals", on Oct. 16, 2017 in the journal, Hospital Issues, Patient Safety. [She had previously lost a young child to such issues in a Hospital] She states: "What exactly is a superbug?" And outlines that these are "In simple terms, a superbug is bacteria that has become resistant to antibiotics." She continues to explain: "No one wants their hospital stay to make them sicker than they were upon admittance. Whether you [or a loved one] are in a hospital for a serious illness or straight-forward surgery, developing an infection from a dangerous superbug can leave you clinging to life.

The bad news: superbugs in hospitals are common and dangerous. The good news: you can take steps to reduce your risk of exposure to superbugs in hospitals. In 2017, The World Health Organization [WHO] released their first-ever list of 12 families of antibiotic-resistant bacteria that pose the greatest threat to human health. The report states that antibiotic-resistance is growing, and the medical community is running out of options. The most dangerous bacteria, classified as 'critical priority', includes a group of multidrug resistant that are dangerous for patients who rely on devices such as ventilators and blood catheters in hospitals, nursing homes, and other settings. These bugs can cause severe, often fatal infections, such as blood stream infections and pneumonia. To make things worse, according to WHO, "these bacteria have built-in abilities to find new ways to resist treatment and can pass along genetic material that allows other bacteria to become drug-resistant as well." Thereupon it states, "How common and dangerous is this? According to the Centers for Disease Control and Prevention [CDC] each year in the U.S., at least 2 million people become infected with bacteria that are resistant to antibiotics and at least [99,000+ in 2017] die each year as a direct result of these infections. How are patients exposed? Unfortunately, patients exposure can occur in many ways. Pathogens move through the air through coughs and sneezes. Medical staff that do not adequately wash hands between patients, then expose others to pathogens. Hard surfaces [e.g., bed rails, nurse call buttons, tray tables etc.] that are not properly cleaned and disinfected on a regular basis pose risks to all who touch them. Additionally, these germs can live on medical equipment, such as ventilators and catheters that are not adequately cleaned. Further on she states: "What can you do as a patient or family caregiver to reduce your risk of exposure to superbugs in hospitals? For airborne pathogens:

"Since there are so many germs in hospitals, act as if all items in a hospital are contaminated. Regularly wipe down hard surfaces with wipes containing bleach, including items that fall on the floor.

Ask all medical staff to wash their hands and/or put on a new pair of sterile gloves before touching the patient. Don't be bashful. Unfortunately, doctors and other medical staff are not washing their hands as frequently as they should. Ask for a private room to reduce the chance of contamination from a sick roommate. If you cannot get a private room, use the room separating curtain, this is especially relevant if the roommate is coughing or sneezing. She continues listing other categories such as: "For pathogens on medical equipment; and Reduce antibiotic overuse" and with many useful and potentially life-saving items from her own experience. What Roberta Carson has attempted to give back is a bitter experience with her young son dying of cancer, and her observations that well can save someone's life.

Of some importance and interest is the List of 12 World Health Organization [WHO] priority pathogens that are critical and without any effective means of control through antibiotics today. The following is the WHO List of Bacteria for which antibiotics are urgently needed:

Priority 1: Critical:
*Acinetobacter beaumannili*, carbapenem-resistant;
*Pseudomonas aeruginosa*, carbapenem resistant;
Enterobacteriaceae, carbapenem resistant; & ESBL-Producing; Priority 2: High:
*Enterococcus faecium*, vancomycin-resistant;
*Staphylococcus aureus*, methicillin-resistant, vancomycin-vancomycin-intrmediate & resistant;
*Helicobacter pylori*, clarithromycin-resistant;
*Campylobacter* spp., fluroquinolone-resistant;
*Salmonellae*, fluoroquinolone-resistant;
*Neisseria gonorrhoeae*, cephalosporin-resistant, fluoroquinolone-resistant;
Priority 3: Medium:
*Streptococcus pneumoniae*, penicillin-non susceptible;
*Haemophilus influenzae*, ampicillin-resistant;
*Shigella* spp., fluoroquinolone-resistant.

This listing is the current demand for new antibiotics to treat and control diseases now without any satisfactory cure from the current antibiotics.

In one recent report on where these pathogens are to be found in a hospital, it is stated that "on any given day about 1 in 25 patients is fighting an infection contracted during hospital care, at an estimated cost of more than $36 billion a year." According to U.S. Department of Labor, 250,000 patients die yearly [2016] from hospital causes. In any event the risk and the cost is high, quite possibly your own life, or a loved one. It always seems to be getting higher every year, The mortuary business must be a very profitable business when linked up with your community hospital.

In a modern number one quality hospital, even a pneumonia patient breathes 20,000 times a day helping the entire closed forced air ventilated hospital try to get pneumonia. Pneumonia was the Number One Killer on Earth prior to Dr. Fleming's penicillin antibiotic in 1945. Isn't this data enough to ask why hospitals are so dirty? And, then I can begin to understand why hospitals everywhere do not want to talk about numbers of 'wrongful deaths' that are their own fault. I begin to wonder just how much is a corpse worth to the hospital, or worth to the mortuary? Can this be so profitable that the hospitals do not want to disclose its value?

The cleaning up the air in a hospital, and clearing out invisible creatures that are dangerous, is a daunting task and it does involve many relevant and related patents across several disciplines requiring investigation in order to structure such a cleaning task. I have divided these several disciplines into separate categories in order to address these issues and properly organize this material. Some categories are easy, and others are lengthy and complex, so here are the basic divisions:

These Categories Are:
I. Acids;
II. Ultraviolet [UV] & UV Lamps;
III. Lasers & Their Radiation;
IV. Filters:
V. Sterilization & Purification, Includes: Heat & Pulsed Lights;
VI. Sensors [Net-Worked or Pressures];
VII. Electric, Electrodes, Electrostatic & Misc.

Now, in the first category are the Virulent and Disruptive Acids that are deadly to germs, superbugs, all small invisible & unseen creatures that infect buildings. Only a few patents are to be found here out of the more than 10 million now issued, of which I am involved in 3 of them [+1 more in PPA].

| Category I. Acids of Note | | |
|---|---|---|
| Patent No. | Date | Inventor/Assignee |
| 5,038,929 | 1991 | Susanne Kubofeik |
| 5,441,622 | 1995 | T. R. Langford/KEW Import-Export |
| 6,315,113 | 2001 | Britton & Woodward/Hetex Co. |
| 9,707,047 | 2017 | Woodward/CIG CO. |

The next Category has Ultraviolet Light, and Lamps, and its Radiation which is a reasonably old art, evident a hundred years ago. In this upcoming category the earliest cited was in 1928, but further investigation will uncover some earlier. The common start for Ultraviolet was as early as 1 940's but since then it became fashionable in the 1980's with increasing usage until recently adjudged an unwelcome light for humans causing aging in the skin and its use has slowly dwindled away today. Other types of acceptable radiation are now available for such use. As in this invention, any use of UV is in a closed system, and is not radiating out, or leaving the sealed casing, there will be no complaint because it does its work well and does kill all of the smallest of creatures and superbugs.

| Category II. Ultraviolet [UV] & UV Lamps. | | |
|---|---|---|
| Patent No. | Date | Inventor/Assignee |
| 2,261,215 | 1941 | L. F. Bird/Trustee |
| 3,418,069 | 1968 | J.J.E.A. Decupper/Detec S.A. |
| 4,229,658 | 1980 | D. L. Gonser/Dentsply Corp. |
| 4,504,445 | 1985 | A. Walz |
| 4,790,862 | 1988 | Namo et al/Matsushita Electric Co. |
| 7,459,694 | 2008 | R. Scheir et al |
| *0119108 | 2012 | Y. Goldshtein |
| *03055787 | 2012 | B. R. Henson |
| 9,707,307 | 2017 | M. Shur et al/SensorElectronic Tech. |

To follow here is a recent invention that certainly does its work—quick and precise—the LASER, developed by Gordon Gould in 1957, and somewhat 'infringed' by fellow scientist and employers as they could. He was denied a patent for c. 30 years while the infringers fought tooth & nail to hold on—but LOST the fight as original records showed and Gould got his patent and damages. The value is shown here in this patent in application is in the final stage in the 'bug battle', then, the Laser will 'fry' the survivors and escape artists in the final best embodiment as shown to follow.

Category III. LASERS & their Radiations

| Patent No. | Date | Inventor/Assignee |
|---|---|---|
| 4,152,625 | 1979 | R. W. Conrad/U.S.Army |
| 6,184,517 | 2001 | T. Sawada et al/YokogawaElec.Corp. |
| *0264512 | 2004 | J. R. Hartlove/NorthropGrumman |
| *0167618 | 2005 | H. Hoshino et al |
| 7,435,982 | 2008 | D .K. Smith/EnergetiqTechlnc. |
| 7,989,786 | 2011 | D. K. Smith et al/Energetiq |
| 8,242,695 | 2012 | T. Sumitomo et al/Ushio+Ener'q |
| 8,309,943 | 2012 | D. K. Smith et al/Energetiq |
| 8,551,399 | 2013 | M. E. Shannon et al/Medizonelnc. |
| 9,368,337 | 2016 | P. S. Antsiferov et al/Rnd-Is-An.Rus |
| 10,111,337 | 2018 | B. A. Strumm et al |

[*= Patient in review to issue]

The next section will cover 'Filters' which have worked well for many years and do have a number of different models to serve cleaning debris from water, fluids, or air. To even consider filtering out the smallest of particulates would seriously slow down its forced air speed and volume to a point of stagnation and disuse. The old standby HEPA does its work efficiently for larger and numerous particulates, but in this invention in application the very smallest of particles at the source of their entrance into a room, or into the air flow, is where this invention is set to work. In other words, this invention introduces the smallest of particles into its cleansing filtering system to be stopped, neutralized, and destroyed totally forever.

Category IV. Filters—All Types

| Patent No. | Date | Inventor/Assignee |
|---|---|---|
| 2,804,839 | 1957 | W. W. Hallinan |
| 4,309,992 | 1982 | M. J. Dodak |
| 4,917,862 | 1990 | Allen & Carol Kraw |
| *0319851 | 2012 | S. Hoglund et al/Honeywell Inc. |
| 9,399,186 | 2016 | H. Welke/EnergyTechTrust |
| 9,552,715 | 2017 | S. Breslin/EDTech Co. |
| 9,623,352 | 2017 | O. Y. Kas et al/EMD Millipore Corp. |
| 9,797,609 | 2017 | S. Sekiguchi/Nikka Micron Co. |
| 9,920,947 | 2018 | S. Breslin/BD Tech Co. |
| 9,981,056 | 2018 | M. Al-Zeer/MAZRA Inc. |
| 10,087,235 | 2018 | G. L. Warren et al/CSLLimited [AU] |
| 10,101,258 | 2018 | S. L. Kaufman et al/TSI Inc. |

[*= Patent in Review to Issue]

Category V. has complexity with divisions of its topics wherein the Sterilization is first, with Air Purification second, and Lights & Pulsed Lights is third. The basic category concerns Sterilization and Sanitation with many ways to achieve such a goal. This category is many years old back into the mid to early 1800's with steam autoclaving, even to today. The varied issues for using steam heat require careful consideration on how best to use it. In modern times chemicals such as alcohol and chlorine can accomplish much in cleaning off bacteria. Cleaning out the air moving throughout an area required much different procedures and the air can contain infectious material which need to be managed and removed. The issue with light is for highly intense white light that has proven its merit destroying bacteria. The light type herein is not the same as Laser Driven Light of Category III, and it is an old art used over time to sterilize milk and food of their bacteria.

Category V: Sterilization, Sanitizing, & Purification: includes with Heat, Lights, pulsed lights, LED's

| Patent No. | Date | Inventor/Assignee |
|---|---|---|
| A. Sterilization: | | |
| 3, 753,651 | 1973 | R. M. G. Boucher/Wave Energy Inc |
| 4,448,750 | 1984 | M. L. Fuesting |
| *0008378 | 2006 | K. Imai et al |
| 7,186,371 | 2007 | D. Watling/Bioquell UK Ltd |
| *0191100 | 2009 | J. L. Deal |
| 9,072,803 | 2015 | A. Sakaki/Pharmabio Corp |
| 0038624 | 2016 | M. D. Krosney |
| 9,943,620 | 2018 | L. F. Bender et al/ControlledPerf.Gases |
| B. Air Purification: | | |
| 3,984,296 | 1976 | J.R.Richards |
| 4,790,863 | 1988 | N.Naruo et al |
| 5,904,896 | 1999 | A. V. L. High/A.R.Grindt |
| *0269254 | 2005 | L. L. Roitman |
| *0253860 | 2007 | W. Schroder |
| *0314164 | 2009 | H. Yamashita et al/SharpKabushiki |
| 9,518,082 | 2016 | D. S. Allison et al/AlderbioHoldings |
| RE46,804 | 2018 | W. Zhang/W. Zhang |
| 9,974,880 | 2018 | M. D. Krosney |
| 9,974,881 | 2018 | J. R. Kim/SeoulVlosysCo. |
| 9,980,748 | 2018 | K. C. Worriflow/LifeAireSystems |
| C. Lights & Pulsed Lights: | | |
| 4,880,512 | 1989 | P. A .Cornelius et al/KollmorgenCorp. |
| *0231496 | 2003 | M. Sato et al/Casio ComputerCo. |
| *9257877 | 2006 | H. Anderle et al |
| 7,068,361 | 2006 | G. D. Cimino et al/Baxter,&Celus |
| *0206554 | 2011 | H. Anderle et al/BaxterHealthcare |

[*= Patent in review to issue]

Then in Category VI for Sensors: Networked or Pressure; the detection of contaminants has to be an issue to rate a listing in this category. The sensor without working inside the new device is not of note herein. The temperature and humidity measurements are for forced air conditioning or heating are not relevant herein, and such issues are external to this new device. Acknowledging and counting of contaminants is useful, and when such is done inside the framework that covers the return air inlet, it would listed here to follow.

Category VI. Sensors

| Patent No. | Date | Inventor/Assignee |
|---|---|---|
| 4,304,996 | 1981 | F . K. Blades/PureCycleCorp |
| 5,394,934 | 1995 | Rein et al/AmericanStandardInc. |
| 6,701,772 | 2004 | Kreichauf et al/HoneywellInc. |
| 6,941,193 | 2005 | Frecska et al/AWI LicensingCo. |
| 7,674,440 | 2010 | A. Martin/Bioquell UK Ltd. |
| *0247396 | 2011 | S. H. Zhang/SmithsDectionInc. |
| *0241601 | 2012 | S. L. Kaufman |
| 9,857,301 | 2018 | I. Nourbakhsh/CarnegieMellonUniv. |
| 9,988,691 | 2018 | Sislian et al/DetonCorp. |
| 10,006,871 | 2018 | S. L. Kaufman/TSI Inc. |
| 10,066,847 | 2018 | W. Zhang/DongguanLifaAirTech. |

[*= Patent in review to issue]

This Category VII is in part a catch all for miscellaneous electrical devices as described to include electrostatic, electrodes, arcs, plus infrared and heat. In this category there is listed only the patents that destroy the infectious material that passes through the device on their way to the main HEPA air return inlet so as the deliver only clean and sterile air to the forced air ventilation system of the building. In the hospital air systems many varied types of infectious material originates in the patient's rooms, treatment clinics, medical procedure offices, emergency care stations and such, and to return through the air inlet to the main ventilation system will clean up all infectious material to leave a hospital free of cross-infections.

| Category VII: All types, including electrical and electronic means, plus infrared and heat. | | |
|---|---|---|
| Patent No. | Date | Inventor/Assignee |
| 2,072,417 | 1937 | Berndt et al |
| 2,258,765 | 1941 | R. F. James |
| 2,482,507 | 1949 | Rentschler et al |
| 3,218,510 | 1965 | P. Schulz |
| 3,926,556 | 1975 | R. M. G. Boucher |
| 4,071,334 | 1978 | Kolb et al |
| 5,667,564 | 1997 | S. Weinberg/WeinProductsInc. |
| 5,993,738 | 1999 | D. Y. Gosani/Univ.AirTech. |
| 6,042,637 | 2000 | S. Weinberg |
| 6,054,324 | 2000 | Sullivan et al |
| 6,149,717 | 2000 | Satyapal et al/CarrierCorp. |
| 6,187,271 | 2001 | Lee et al/LG ElectronicsInc. |
| 7,767,169 | 2010 | Snyder et al/Sharper Image |
| 8,295,690 | 2012 | Brooke et al |
| 9,504,255 | 2016 | Y. Cai/NMS Tech Ltd. |
| 9,808,808 | 2017 | Wen et al/Univ.of Washington |
| 9,919,816 | 2018 | F. Tenegal/Nanomakers[France] |

[All items are +++'s unless noted otherwise]
[*= Patent in review to issue]

Now all of the Categories are finished and they list 100 U.S. Patents that really support the main issues of this application. These cited patents do represent the most relevant of the prior art as is listed as references in the opening pages as both in patents issued and application for review prior to issue as a full utility patent. There are prior art references of 597 patents in the opening pages with 27 International Classes shown, and 47 classes of the CPC under the new AIA designation, and 27 separate classes of USPC, and 30 World Patents. All of these references [+Bibliography with 10 books] show an effort of more than 800 items in review out of the 12,000 found in overall class search of patents. The rationale behind such a lengthy search is that this patent in application covers a lot of items when forming up its procedures to try to totally Clean Up The Hospitals. In the 'Summary of the Invention' with Claims and Figures these efforts will become obvious that this effort and these many disciplines are required to gain a Letters Patent.

BRIEF DESCRIPTION OF THE DRAWINGS

FIG. 6 shows a hospital double bedroom wherein unseen colonies [26] and germs [some infectious] remain safe when hiding underneath the beds [2] and tables [12].

FIG. 7 shows FIG. 6 wherein the arrows [11] mark the pathways that HEPA [4] uses to move its air over and under beds and tables and into the air return [6] vent.

BRIEF DESCRIPTION OF THE DRAWINGS

Figure 10:
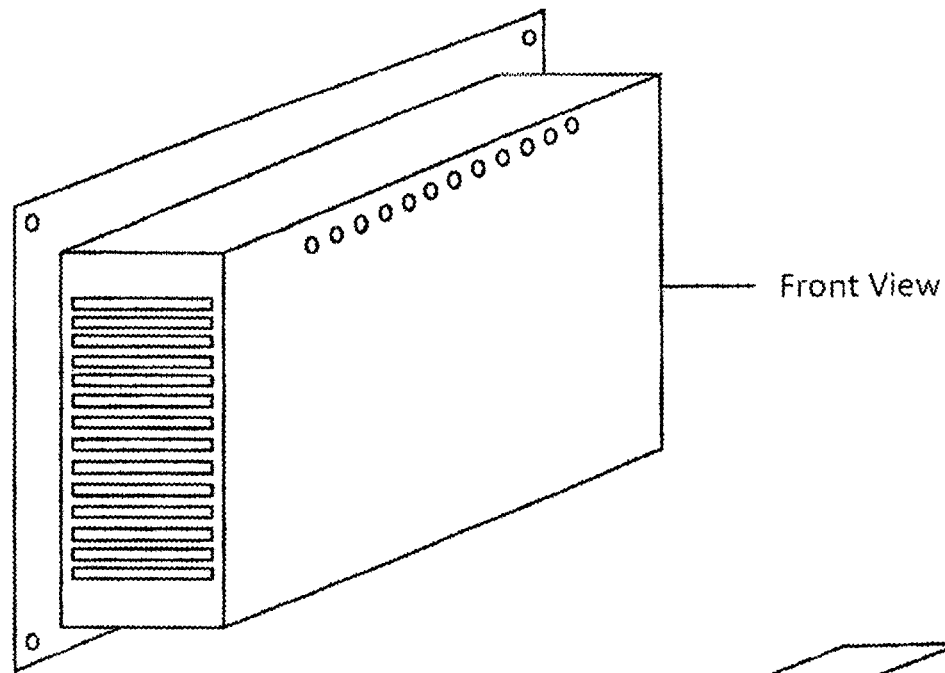
FIG. 10 shows the interior front view of a typical smallest particulate absorber that will be placed over the normal room return air vent.
Figure 12:
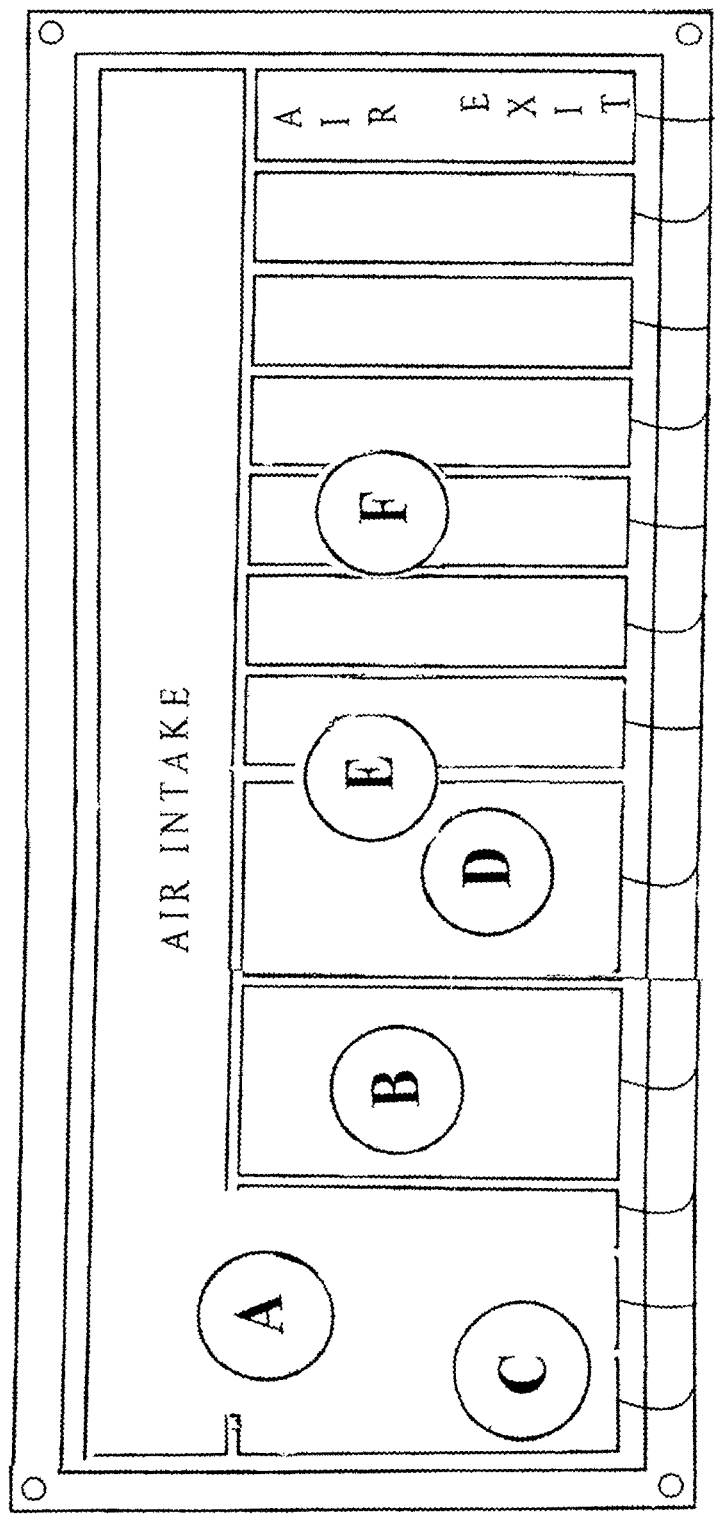
Figure 13:
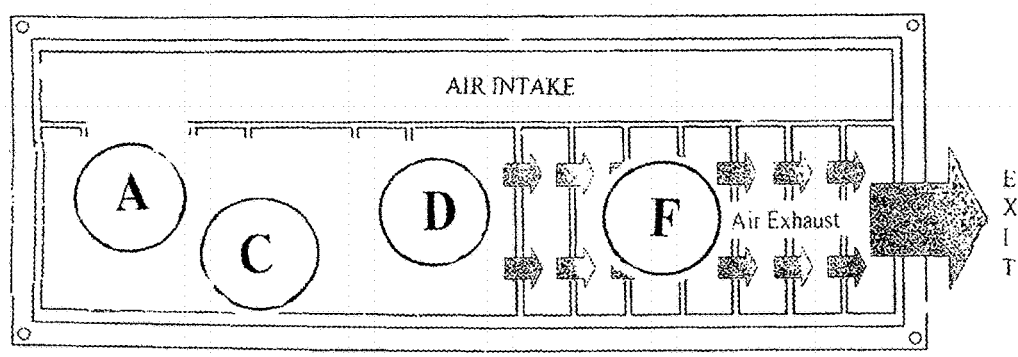

FIG. 12 shows a frontal view as shown in FIG. 10 wherein all possible Sections are shown that can effectively destroy the infectious material as outlined herein in the patent in application and briefly listed below:

FIG. 13 shows another frontal view as in FIG. 12 before with Section A, C & D in the initial chamber to obliterate and stop all infectious material that passes from a room into the return air vent; wherein in the Section F all material is absorbed and stopped by dense charcoal filters [including copper particles] of a long lasting efficacy [6 months or more].

Figure 14:
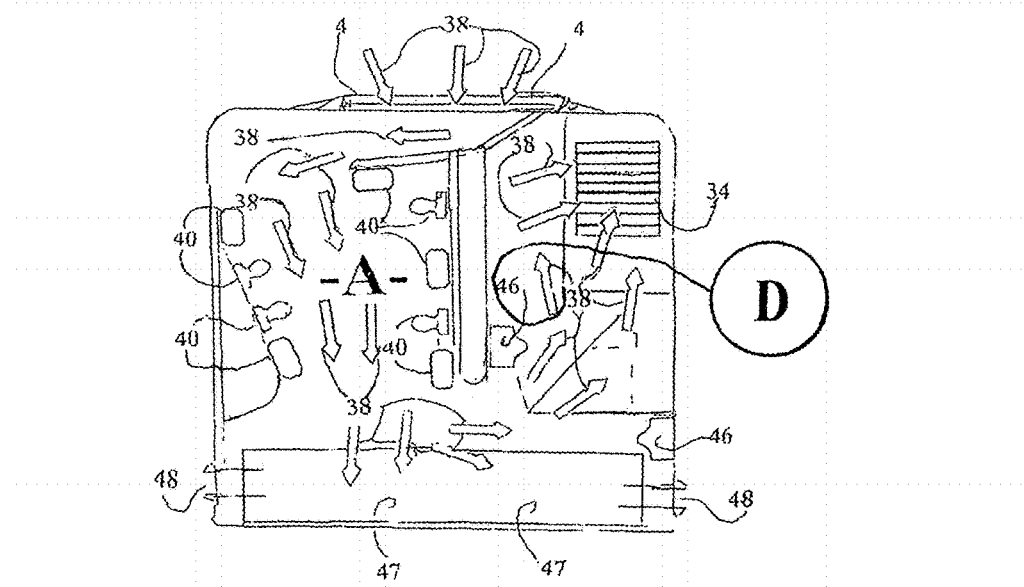

FIG. 14 shows a another style of wall mount displaying 2 separate Sections of Saturation Chambers as A of UV-C, and D of Ozone and shown with directional arrows marking the movement of air. The Sections E and F can be positioned at air exit locations, if deemed necessary.

A=Ultra-Violet Saturation Chamber, in the 'C' type the radiation passes through the flesh, stopped only by a human bone, to cook the flesh with morbid sunburn and oftentimes fatal Melanoma Cancer.

B=Vapor from Chemical Dissolvent out-gassing at room temperature.

C=Laser [light amplified stimulated emission radiation] gives high heat beams quicker than light to destroy invisible creatures.

D=An ozone chamber from a device that saturates air with deadly ozone.

E=A high voltage electrostatic screen that obliterates insects and germs.

F=Charcoal Filters designed to disintegrate and stop infectious material.

Of Note: As these devices can be adjusted and assembled for local conditions at a Hospital; as claimed herein, an intake and an exhaust particulate counter sensor will quickly yield a physical count of how effective such a device would be, and adjustments can then be undertaken to correct any issues that are seen.

| INDEX TO FIGURES TO FOLLOW: | |
|---|---|
| REF. NUMBER | BRIEF DESCRIPTIONS |
| 2 | Hospital Bed |
| 4 | Intake Air Vent |
| 6 | Exhaust Air Vent |
| 8 | Wall Lights |
| 10 | Ceiling Lights |
| 11 | Arrows Showing Air Movement |
| 12 | Small Convenience Table |

-continued

| INDEX TO FIGURES TO FOLLOW: | |
|---|---|
| REF. NUMBER | BRIEF DESCRIPTIONS |
| 14 | Over Bed Table |
| 16 | Sleeping Couch |
| 17 | Sealed Viewing Window |
| 18 | Large Comfortable Chair |
| 19 | Small Convenience Chair |
| 20 | Large Door [36"] |
| 22 | Kitchen Area |
| 23 | Bathroom |
| 24 | Storage Closet |
| 25 | Tub & Shower |
| 34 | Return of Air to HEPA |
| 38 | Arrows Showing Air Movement |
| 47 | Cleanout Tray |
| 48 | Vacuum Access for Cleanout |
| A + 40 | UV-C Saturation Chamber |
| B | Vapor from Dissolvent Acid |
| C + 46 | Laser Beams |
| D | Ozone Chamber |
| E | Electrostatic Screen |
| F | Charcoal Filters |

Figure 11:
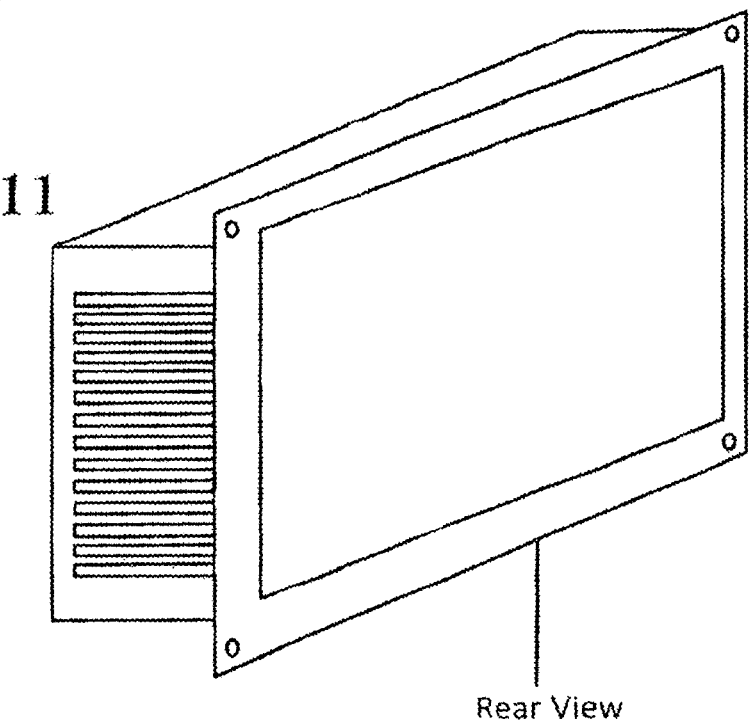
FIG. 11 shows the rear view of FIG. 10 which will be placed tightly against the HEPA return air vent in order to process clean all air leaving the bedroom.

Of Note:
FIGS. 10 & 11 show a typical return exhaust air device that installs on the wall over the HEPA [forced air ventilation system] vent that gathers up the room air to be re-circulated over and over again.

SUMMARY OF THE INVENTION

This invention in application is designed to make the buildings with forced air ventilation systems safe and free of disease and contamination from the circulating air in the building. Mostly, the hospital causes the most problems in this manner as it can seriously disable or even kill people with the diseases it routinely carries in its air. The average and normal business center with a closed window forced air system does not possess any disease or contaminate in any strength or number to bother anyone inside the building, but the hospital does have numerous airborne infections and disease for every person inside the building.

The serious question is, where does such an infection get to you? It is already inside the hospital, is how and why. No other property has so many dangerous diseases as does the hospital. Few people have reasoned out how such dangerous disease and infections are routine all over the building. Few have reasoned out why new nurses are always being sought to work there. If the number of people who staff the hospital were sufficiently detailed as to their health over the years, there would be good reason why they left their chosen work, and why the turnover is high in the hospital staff and working people over the years. The statistics and much of the reasons has been outlined in the prior section on 'Background of the Invention' and in this section an answer will be expounded to solve and control this puzzle.

If you want to catch pneumonia, go to the hospital because that's where you can find it. Where does this disease come from? Pneumonia was the Number One Killer in the known world until 1945 when penicillin was introduced by Dr. Fleming of England into the medical community. The use of antibiotics saved many lives over the years since, and has been depended upon to cure even minor discomforts in modern times. Today an over dependence and use of these antibiotics has given rise to a new threat, the super-bugs, that are not responding to normal antibiotic treatment as they have in the past and have adjusted their reaction to offset these upgrades.

Currently, the medical community is stymied and has become much more cautious and selective in the use and dependence on traditional antibiotics which in many cases has now become totally ineffective and useless as a medical treatment. The modern closed air ventilation system in point of fact helps spread these new 'super' germs and diseases all over the hospital complex, Airborne infectious disease comprises the best means to transport virulent contaminated air throughout a building, including hospitals, using the forced air ventilation systems. These airborne infectious diseases also comprise the best means to transport such virulent contaminated air with its disease from one infected patient to everyone in the building, especially hospitals.

These airborne infectious diseases which have these unseen and invisible creatures which will pass right through the existing filters used to clean up the contained air that re-circulates in the building complex. In the High Energy Particulate Absorbed System [HEPA] long established and in use universally since the 1940's, it can be made to use closer and tighter filters, but such action would slow up the delivery of the requisite forced air to become unacceptable in the ventilation that is required and necessary to keep the building occupants breathing with enough oxygen to function at their work.

What the HEPA does well is to serve adequately the large areas of a modern hospital complex, or office building, or any closed forced air ventilated building, in its normal service over thousands of feet in distance and very high volumes of air ventilation required to serve these long distances for every minute of every day continuously year after year, as intended. This ventilating method requires its air being returned to be re-circulated again and again for many years, and thus, it is gathered up and returned without concern, without regard, or any treatment into its main forced air ventilation system for many years.

This invention, the smallest particulate absorber, can solve the return of contamination and disease back into the HEPA System by absorbing and stopping the automatic, non-thinking, return of the dangerous infected air into the main HEPA ventilation system. This smallest particulate absorber device comprises a means and method to absorb 0.3 microns or smaller particulates that can render all closed building forced air ventilation systems, especially hospitals, to have clean and safe air ventilation for all occupants within the building. The smallest particulate absorber further comprises a device that will remove all airborne particulates irrespective of size prior to their entry into the return air vent so that all air being returned to the main forced air ventilation system to be re-circulated throughout the entire building system will be safe and clean.

This invention as presented in this patent in application would solve this dilemma by properly and safely cleaning of the returning air to the main ventilation system as the space that this invention serves is small, typically just a patient's room, and not a whole building, or an entire ward or floor.

This device can manage even the thousands of infectious germs and diseases all of the time, without undue difficulty, and can do this every day for months and years. When the patient's room air is just returned without concern or treatment, everyone in the building can catch a new disease. This smallest particulate absorber within its device further comprises to seek to render all closed buildings, including hospitals, with the forced air ventilation systems, in as much as is possible to have this device installed, then to have safe and clean air provided to all patients, medical staff, daily workers, visitors, and the public who have entered the hospital.

You cannot clean up the main HEPA type ventilation system as it does its work well and performs as constructed, but you can return to the HEPA system safe and clean air for the ventilation system to use all over the hospital, or any building, with forced air ventilation circulating in a tightly closed modem building where the windows will not open to get outside air. This invention in application, the smallest particulate absorber, [named after the big system-HEPA] shall comprise that all airborne particulates are to be removed, and subsequently neutralized, disinfected, and destroyed with a safe disposal prior to their entry into the existing return air vent that usually would just be returned without concern, or treatment, into the main forced air ventilation system.

This smallest particulate absorber further comprising a device that all airborne particulates shall be removed and safely disposed of prior to their entry into the existing return air vent for re-circulation, and this device with the means and method shall effectively eliminate most cross-infections [aka 'nosocomios'] that is oftentimes acquired in the existing hospital environment and that has proven disabling, and often fatal in an unclean dirty hospital. It seems that the smallest particulate absorber comprises a device that shall return safe and clean air to the main forced air ventilation system free of infectious material including, but not limited to, particulates, pathogens, viruses, microbes, bacteria, germs, fungi, mold spores, dust motes, and as possible, all unseen and invisible creatures.

What are we saving the patients in their rooms from? Is such an onslaught of unseen and invisible creatures dangerous, or possibly fatal? Recent studies and reports of cross-infections show large numbers of deaths and unwelcome disease in hospitals. While some of such dangers are to be expected in routine hospital issues, the no-somos deaths are very high; in the hundreds of thousands: [1] Dept. of Labor=250,000; a recent medical research=440,000; CDC of Atlanta=721,000, a recent observation this current year=1,250,000.

In a report by David Day from his book, "The Environmental Wars" Ch. 8.2: Bacteria as the dominant form on Earth, pg. 173. It is stated: "Formidable and numerous as insects are, however, if we consider all life forms on this planet, we must conclude that [our] Haldane's perspective was not quite radical enough. [J. B. S. Haldane endorsed insects, especially beetles as dominant, pg. 171] "While insects are without doubt the most numerous and successful invisible creatures on the planet, of the estimated 3,000 quintillion [3+33 zeros] living things, [& of these] 75% are bacteria. These unicellular micro-organisms, the minutest and earliest forms of life, can survive the most extreme conditions of heat and cold. They can be found in the deepest ocean and furthest stratosphere. Even in the event of a nuclear explosion, they have survived a radiation dosage 10,000 times stronger than that which is fatal to humans."

Further in his article he describes microbes as, "Microbes are the most formidable, ruthless, and effective of killers. Adaptable and wily beyond all cerebral intelligence, they are genetic generals quite without compassion." [pp. 173-4, The Environmental Wars]

Why have the operators of hospitals let the cross-infections abound? With new 'super-bugs' now entrenched in hospitals, and myriads of pathogens that transport disease, invisible microbes and viruses, and unseen bacteria under every bed, table, chair, couch, kitchenettes, bathrooms, window shades and curtains, and behind every picture or sign, where they are never cleaned over the years. These germs can lurk undisturbed until they over-colonize, or get hungry, and must move, by floating away on the air into the HEPA System. They become airborne to go hunting for a new patient. These germs have no legs or arms to move with, yet can move around throughout the hospital by floating into the return air vent of the forced air ventilation system. Then these unseen and invisible creatures will be scattered all over the closed building, available everywhere to infect or disable anyone they can reach.

This invention in application will stop these infectious unseen and invisible germs from reaching anyone, and anyplace, in the hospital ever again. The newly equipped hospital can claim to be the safest and cleanest hospital in the World, and assuredly the safest and best in their area. Patients will vote with their feet. Would you, or anyone that you know or love, prefer a Safe Clean Hospital, or an unsafe, dirty hospital? A wrongful death by an unclean, dirty hospital from 'cross-infection' [the 'no somos'] can bring a law suit and judgment against the hospital owners.

In this invention in application the smallest particulate absorber shall be located over the return air vent by a device that will separate and remove all said particulates prior to the air being returned safe and clean to be re-circulated throughout the building in the main forced air ventilation system. These smallest particulates further comprise a device in that all airborne particulates, even those free to float in the ambient air, and are anti-gravitational, will be removed to be neutralized, disinfected, destroyed, and to be safely disposed of, prior to such safe and clean air being returned to re-circulate in the main forced air ventilation system.

This smallest particulate absorber further comprises a device that provides the means and method that can absorb 0.3 microns or smaller particulates from a forced air ventilation in a building comprising these operations singly, and in combinations, but not limited to these as stated: [a] absorb all smallest particulates of the forced air ventilation system; [b] absorb all sizes of particulates as is possible; [c] disinfect all said particulates; [d] neutralize all infectious particulates; [e] destroy all infectious particulates safely; [f] destroy all germs and microbes safely; [g] destroy all unseen and invisible creatures safely; [h] destroy all pathogens, viruses that enter said device; [i] destroy all bacteria and fungi that enter said device; [j] destroy all mold spores and such that enter said device; [k] return safe and clean air to main forced air ventilation system; [l] return air free of infection to main forced air ventilation system; [m] gather all destroyed material for safe disposal; & [n] gather all said material for routine safe removal.

The smallest particulate absorber as presented in this invention in application shall comprise a selected embodiment that presents the best means to eliminate all noxious airborne infectious material within the device prior to its return to be re-circulated in the main forced air ventilation system. If the self-evident over-reaching cross-infections are permitted to continue without concern, due consideration, or some method of treatment, then hospitals will continue to be dirty and pestilent places that allow and foster wrongful deaths and undue disabilities as virulent contaminated air is exchanged from room to room upon their paying patients who are their guests, and upon their medical staff and daily workers, paramedics, nurses, doctors, and the public. Airborne infectious disease comprises the best means to return virulent contaminated air from room to room without concern and treatment until this novel, new, and not-obvious invention is employed.

Airborne infectious disease comprises that virulent contaminated air containing microbes, pathogens, viruses, bacteria, germs, fungi, mold and unseen invisible creatures that are not to be absorbed and filtered out, as being too small to be detained by the rapidly moving air of the main forced air ventilation system. Airborne infectious disease further comprising that all forced air buildings such as office type, commercial, industrial, government, executive, legislative chambers, courts, schools, universities, libraries, apartment buildings, and even residential homes are not protected from the rapidly moving air of the forced air ventilation system and accordingly would not be able to protect their occupants from direct exposure and catching an infectious airborne disease.

Airborne infectious disease do comprise hospitals that can spread contaminated air everywhere in the hospital without concern if without our new invention being installed throughout, from one patient to everyplace in the building, the emergency stations, clinics, treatment rooms, doctor's offices, nurses stations, medical staff, daily workers, cafeteria personnel, lab workers, parking attendants, other patients, reception areas, visitors, and the public. Thus, airborne infectious disease exists in modem hospitals as it goes everywhere unfiltered and not treated throughout the building to refute the claims of a clean and healthy hospital with the facts that show it is a dirty and unsafe hospital and is a danger to all.

This new invention, the smallest particulate absorber comprises a device that will clean the air from the patient's room in the room as its source of said infections in our device that is placed over the normal return air vent in order to treat and disinfect the room air before it can reach the normal return air vent. This is the only way to identify and remove all particulates and the unseen invisible creatures before they return normally into the main air ventilation system. In this manner nothing is disturbed or interrupted in the normal circulation air ventilating the entire building. This device is therefore inserted into the return air stream, and it does not interrupt anything in the normal operation of the HEPA System which is very efficient and capable of ventilating its entire building. First things First, we will make the room air safe and clean, and then pass it back into the HEPA System.

It is the Sections of the Device that contain the means and method of treating and cleaning the room's air. These sections compose this invention in application, when properly assembled into this device, as will be outlined now. Variations for their best efficiency and usage will be shown in the selected embodiments that are to follow. In the first embodiment are sections with [A] the ultraviolet saturation chamber, plus [B] the acid vapor means, and [C] by the laser beam sweeps, any and all of which can and will destroy all germs and particulates prior to any air being returned, albeit safe and clean, to be re-circulated in the main forced air ventilation system.

This smallest particulate absorber further comprising in the selected embodiments of said device that are chosen shall comprise sufficient protective shielding that is effective preventing emission of radiation outside of said device when in operation. This provides a minimum safety precaution as no operation or process will give off any undue radiation hazard, but it seems good sense to be careful and safe.

The first section is a saturated ultraviolet radiation chamber wherein there will be no shadows as often in a patient's room, nor one individual blocking another, or being underneath furniture, or just out of sight. It will be possible as the ultraviolet radiating rays will be everyplace throughout the chamber. No saturation such as this chamber will provide, is possible in the open air and spaces inside a room, and every particulate will face the effects of this first section. The ultraviolet radiation most effective is UV-C and of short wavelength of from 80 nm to 253.7 nm which disturbs the microbes nucleic acid and they are no longer infectious or can reproduce, then soon die. [source: FIG. 2 Prior Art] This further explains more of why this operation will do most of the sanitizing work, a quote from George Chabot, PhD, CHP, states: "The shorter-wavelength, higher-energy UV radiation associated with the UV-C category is very strongly absorbed by most organic materials. Thus is why the common 254 nm sources have become so popular for germicidal disinfectant applications. The strong absorption by organic molecules, including DNA [& RNA], leads [in] to severe damage to the molecule and the organism's reproductive processes, leading to the death of the molecules." [source: Google Internet: 'Effects of UVC on humans'] This helps explain why in the room there are many places to hide and avoid being cleaned out; but in a specially equipped chamber there is NO Escape. Probably, all of the unseen, invisible germs and particulates will be extinguished by this means.

The second chamber follows with an acid vapor [optionally, an acid bath that all air must pass through] that requires no electricity to operate, based on my earlier work in U.S. Pat. No. 6,315,113 & 9,707,047 in this field. This acid bath and its vapor are designed for the non-electric areas in remote locations, usually in primitive medical care buildings with open windows and open ventilation wherein this technique can be effective, It can be possible in the embodiments to follow that some solar electricity can provide a limited service of the ultraviolet system with low-electric UV diodes, plus one Laser Beam service.

The third section has Laser [Light Amplification by Stimulated Emission of Radiation=LASER] that uses a continuous beam array to obliterate any and all substances in the air that the Laser is aimed toward. This Laser has been much feared by the military forces in recent years for its very unusual methods and techniques. In this invention in application the Laser devices serve to eliminate any final remaining particulate, or unseen invisible creatures that did survive then to pass safe and clean air into the return air vent for HEPA re-circulate in the hospital, or in any forced air building.

In the Figures to follow, the first six are prior art that show how pervasive the use of UV-C has become. A development from this new application of UV cleaning of germs was the tanning business using UV to darken outer skin so that young people would look 'pretty'. Soon tanning salons wherein a person could lie down in a casing to receive 'tanning' with UV radiation. A motto for such application should have been: "Die Young & Look Pretty".

This invention at least uses a separate shielded chamber to obliterate the unseen creatures and particulates, and pick the germs up airborne as they move on the room air toward the return air vent. This device will obliterate all of the germs that move, even when from underneath the furniture out of sight, because among these are the infectious and dangerous germs that can kill. All prior art does cite the effectiveness of UV-C at destroying surface germs, in the FIG. 2 of Prior Art, the patent does state: "Surface disinfection of patient care areas is a key factor in the constant battle to reduce or eliminate Hospital Acquired Infections [HAIs], also known in the art as 'nosocomial diseases or infections. Increased evidence published in scientific literature confirms that '*Clostridium difficile*' MRSA, VRE, Aeinetobacter *baumannii, 'Bacillus subtilis*' var. *niger, Bacillus anthracis* Sterne, and influenza are transmitted via environmental surfaces and air" [source: U.S. Patent in Application #2012/0305787, cited in Paragraph 0002, cited in FIG. 2 to follow].

"Where does the air come from? On the surface of furniture, or underneath the bed, tables, or chairs also? Is this novel, new, and non-obvious invention needed, or NOT?

The First Embodiment contains:
Section A—Ultraviolet Saturation;
Section B—The Acid Vapor & Bath; &
Section C—LASER as Final Elimination.
The Second Embodiment contains:
Section A—Ultraviolet Saturation:
Section D—Ozone Chamber; &
Section C—LASER in Two Beams.
The Third Embodiment contains:
Section A—Ultraviolet Saturation;
Section D—Ozone Chamber;
Section E—Electrostatic Screen.
Section F—Charcoal Filters
  [with Copper Particles]
Of Note: An optional fan may be used if return air movement becomes too slow to process expediently.

If electric power often fails, a model containing rechargeable Lithium-Ion Batteries can be supplied to assure continuous operation.

To ascertain that the novel, new, and non-obvious device will perform its work & wherein all those concerned can realize & understand that this new device is working, an intake particle counting sensor will be located at the air entry section versus a similar particle counting sensor which will be located at the exit area that passes the processed air back into the return air vent serving HEPA. The efficiency of this device will be seen in the heavy load of intake particulates versus the few in number that exit into the HEPA air return vent. This two-step operation will show just how well & clean the return air can be. As a note herein, the return air can be much slower in a smaller space like a patient's room, or a clinic, than can the overall, larger ventilation system operate in as it must move air & oxygen throughout the entire building continuously all the time. Another benefit in the smaller individual spaces that will arise in treating specific germs, or diseases, more capably & directly with slower air movement & specific identified targets. It is thus, a WIN-WIN situation for every ones' benefit.

Another inclusive benefit can be available wherein light emitting diodes [LED's] can be positioned to give a visual indication of how a section, or an area device, is functioning which will allow replacement, or maintenance, as needed In addition to the LED indicators, actual switches for Off-On Functions will be available to allow for removal or replacement, temporary downtime, or repair, or maintenance of a Section that is selected.

Another great & available option can be purchased would be a battery pack with long lasting & powerful Lithium-Ion [rechargeable & replaceable] Batteries. Another option can be a complete, independent electric power system using The Vapor Motor which is Clean & Green [It uses NO fossil fuel, it has NO tailpipe to pollute, it uses NO oxygen, & it is in a tightly sealed casing]. This independent & complete system would power a generator, or alternator, & would come with a 6 plug in receptacle to use for other power needs.

In the closing sections for this Patent in Application to follow are the claims, figures, abstract, & detailed description of the drawings that will complete this application.

As I am now 85 years old, I will now ask for a Letters Patent be considered to be granted for the New & Novel, & Non-Obvious Invention.

DETAILED DESCRIPTION OF THE DRAWINGS

In FIGS. 1 through 5 that are Prior Art, the reasons these drawings are included is that all of these drawings show the most modern & accepted way to clean & destroy bacteria & germs in hospital rooms by sterilizing the top visible side only with their surfaces that are seen & reached comfortably. All of the counters, tables, chair seats, shelves, bathroom sinks, toilets, tubs & showers, all items that can be reached. Obviously with strong disinfectant all the bacteria & germs are killed, but the patient's room is not clean & safe because most of the infectious material is out of sight & underneath these cleaned surfaces.

The microbes & their infectious cousins, called pathogens, are perhaps 3 billion years old & they are not stupid. They have survived without legs & arms like we have [they are anti-gravitational & float in the air], & they reproduce many times a day to be able to adapt to new conditions in their lives. If you kill them on the surface, they go underneath & out of sight to live. They go out of reach by human means, & they continue their life.

In our current times a new threat has emerged, the corona virus [aka, COVID 19]; but there are many more viruses & bacteria out there that are available to come & infect people over the years ahead. SARS [aka Severe Acute Respiratory Syndrome], a close type of COVID 19 virus, & a killer in its own right, is another example seen in recent years, There are many, many others, perhaps hundreds & more, even thousands, that are similar, & waiting to emerge to sicken & kill people. It has been reported that over one million patients in the hospitals in the USA are killed every year now from "cross-infections". Also, each year, many hospital patients are able to walk away from the hospital carrying their new 'Cross-Disease' with them [perhaps, 600,000] to live with at home or at work, & hopefully to cure such over time [or, not].

This new COVID 19 is however, very different, IT COMES TO YOU AIRBORNE. While some people are infected by direct contact, the Corona Virus travels everyplace airborne. Because Air Bourne Transmission is what this invention does take care of every minute of every day forever, so you can live.

In the Figures #6 to #14 to follow, how this invention works is shown, so consider these Figures carefully to understand, why it is unique & important today.

In the Prior Art shown here cleaning the surfaces will not affect this new virus very much & this COVID 19 will spread all over the hospital because it is airborne, & it will go right into HEPA to move everywhere to reach out to all medical staff, lab workers, orderlies, nurses, doctors, patients, everywhere. Any infectious material, especially known airborne viruses, will reach everyone, the public, the visitors, the reception area, the delivery people, the florist, the cafeteria workers, the laboratory workers, the office workers, the clinics, the patients, the sick & infirm, the family of the patient. The airborne virus will reach EVERYBODY. Everyone in the building will be reached by means of the forced air ventilation system [HEPA]. So, this novel, new, & non-obvious invention can stop this catastrophe render safe & clean all hospitals that use this invention.

In FIG. 6 there is shown an empty double bed [2] hospital room with all basic equipment in its place, & this view is to compare to the next view of an equipped & active room condition in FIG. 7. Both views are the same with the incoming air vent [4] in the ceiling with two matching UV lights [10] to keep the top surfaces clean of infectious material. The incoming air is shown with arrows [11] as the air passes through the patient's room over & under every object. The two beds [2] & their small adjacent tables [12]

both show the top surfaces [2 & 12] as well as the under sides where infectious material hides untouched [26] on both beds [2] & tables [12].

In FIG. 7 the beds [2] have wall lights above [8] to see with, & arrows [11] to show the random movement of air in the patient's room with air movement [11] BOTH WAYS over surfaces & underneath out of sight & untouched, as the air [11] moves everywhere through the room, & out into the return air vent [6] to go back to HEPA, the forced air ventilation system. When viewing these two Figures try to realize how extensive the HEPA ventilation system seems & that it does reach everywhere—above & below—& at high speed.

Figure 1:
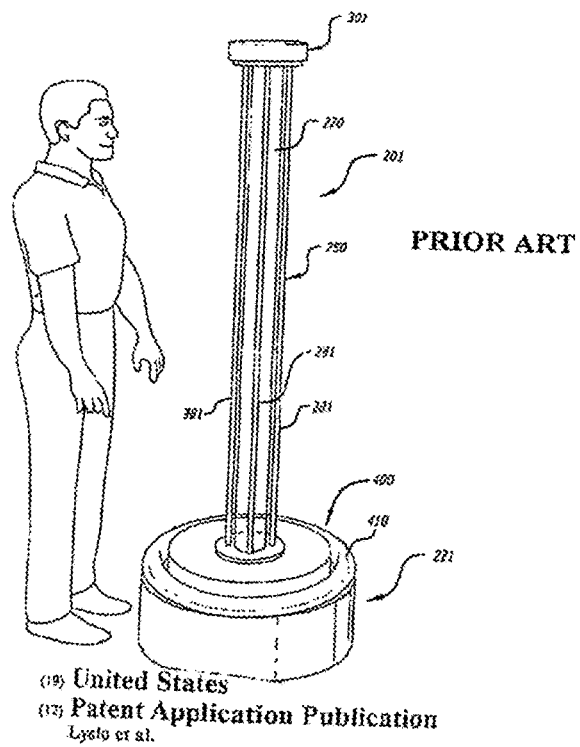
FIG. 1 [Prior Art] shows a person standing in front of an Ultraviolet [UV] Tube Light, being disinfected by its radiation.
Figure 2:
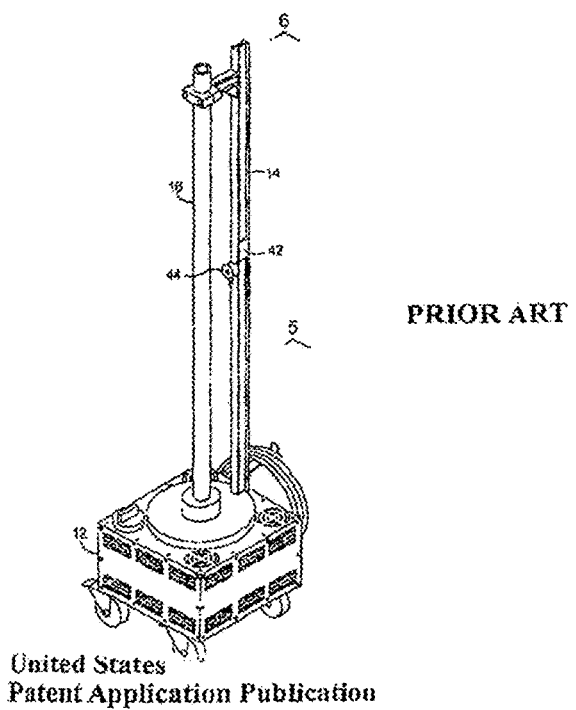
FIG. 2 [Prior Art] presents a similar device that may be rolled around from room to room to disinfect by radiation means.
Figure 3:
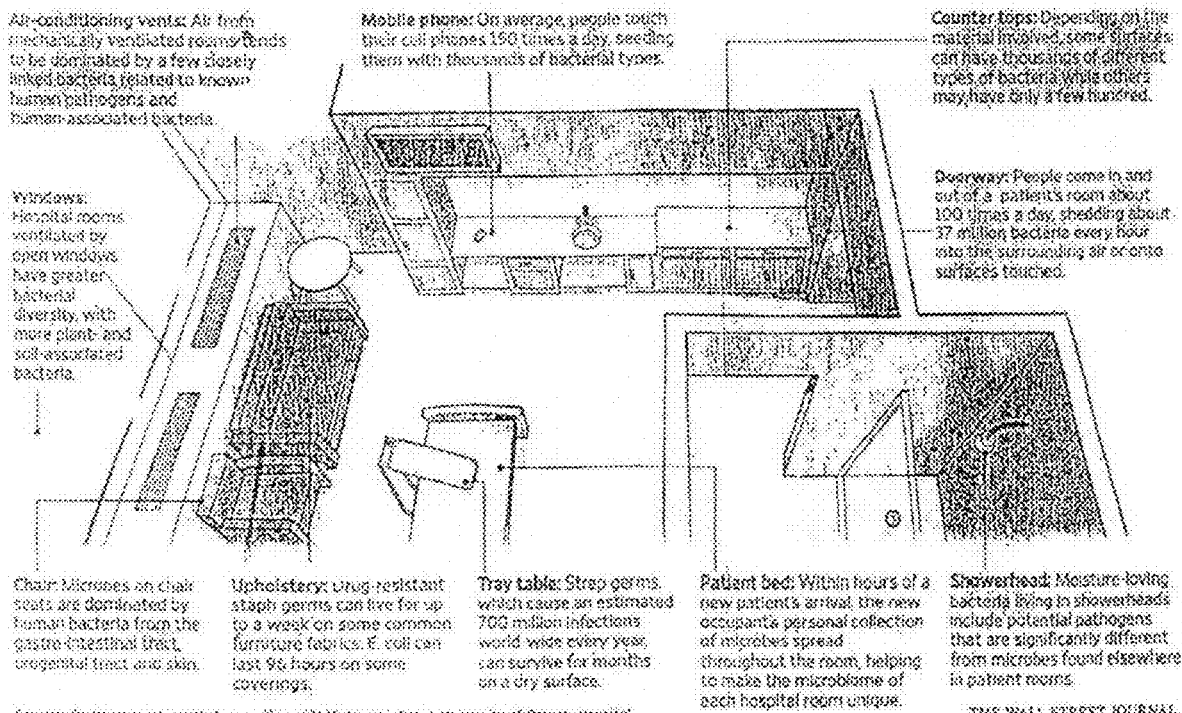
FIG. 3 [Prior Art] displays an article, "Bacteria by Design", written by Robert Lee Holz that shows "Researchers Map Where Hospital Pathogens are Lurking".
Figure 4:
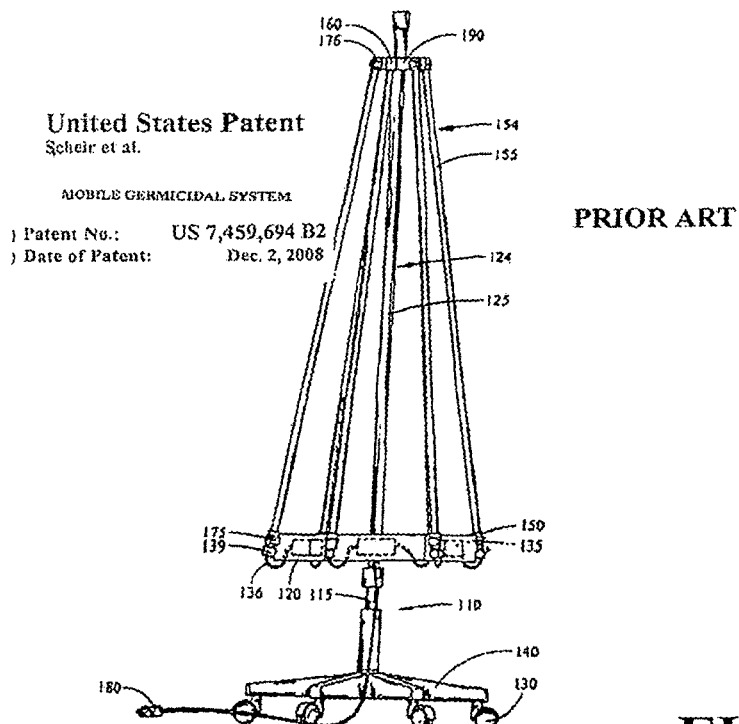
FIG. 4 [Prior Art] displays another device that may be rolled around from room to room that may be opened like an umbrella to radiate and clean an entire room.
Figure 5:
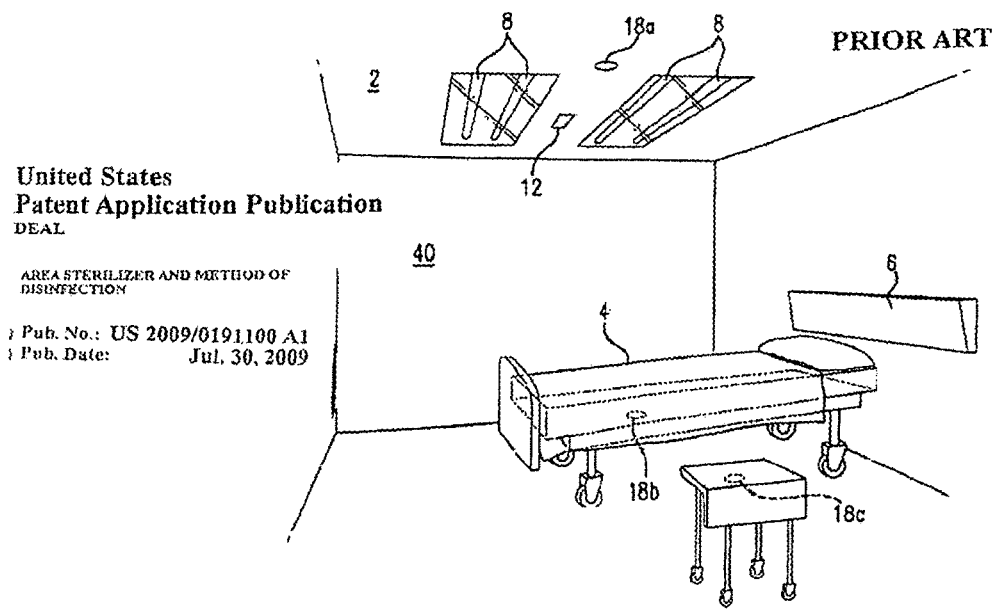
FIG. 5 [Prior Art] shows a single bed hospital room with overhead UV Lights [8] to keep the room radiated and disinfected.
Figure 8:
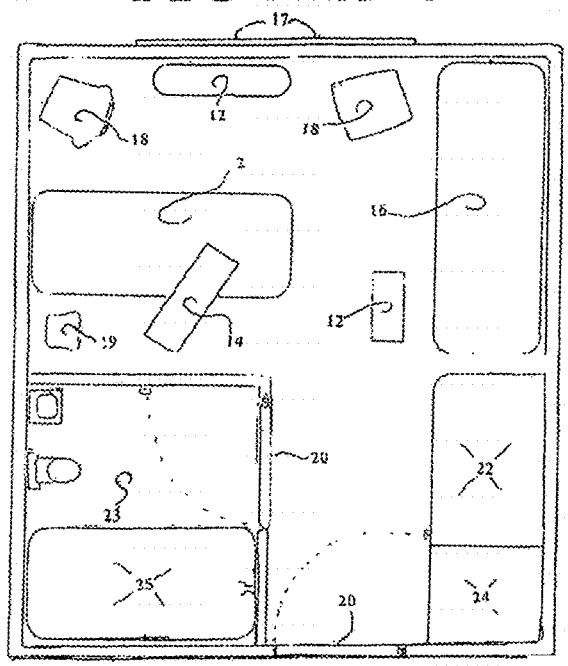
FIG. 8 shows an overhead perspective view down into a single bedroom with a guest sleeping couch [16], chairs [18 & 19] and tables [12 & 14] in their locations.
Figure 9:
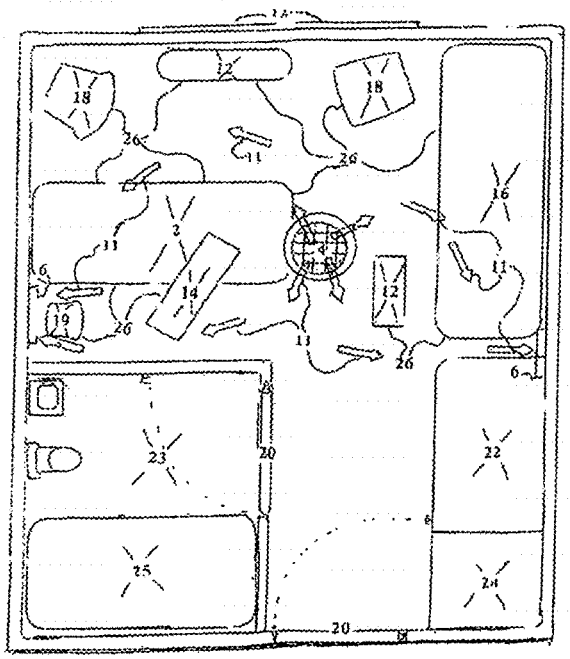
FIG. 9 shows the same bedroom view wherein arrows [11] mark the pathway for HEPA air to move around the room into the air exits [6 & 6].

In the FIGS. 8 & 9 this composite is again shown wherein the FIG. 8 room is shown empty, & in FIG. 9 shows the movement of random ventilation air [4] is marked by arrows [11] that pass both underneath objects [26] & over their top surface on its way into the two return air vents [6] for its re-circulation over time continuously by HEPA. The identifying marks are the same as prior FIGS. 6 & 7 wherein the beds [2] & over bed table [14] used to feed meals to the patients. The convenience kitchen [22] & storage closet [24] are across the room from the beds to facilitate food services. Visitors & family will find several chairs [18 & 19], tables [12] to use for visits. An overnight resting couch [16] & bath room facilities [23] with a tub & shower [25] are within the patient's room. Large wheel chair [36"] accessible doors [20] & an outside view window [17] complete this patient single bed [2] room.

What is to be learned from this set of patient rooms as shown typical to a hospital is that these type rooms are filthy & dirty & disease ridden all of the time, & no amount of surface cleaning will protect the patient from diseases & germs every day. If a disease is available, it is to be found in a hospital & freely administered to every person—patient or visitor—or staff member or nurse—or doctor or intern—janitor or delivery person—everybody all day [& night] long forever. The only way for a hospital to rate high is to cure this problem & become clean & green to treat every one safely.

In FIGS. 10 & 11a typical device is shown—front & back—that fits on a wall over the forced air vent of the ventilation system [HEPA].

In FIG. 12 is shown a diagrammatic side view of a typical device just viewed in FIGS. 10 & 11 & that locates by letter each section chamber that is installed in this device shown. Each section has been previously outlined herein, & briefly as follows:

A=Ultra Violet C type [UV-C] Saturation Chamber;
B=Vapor from Dissolvent Acid;
C=Laser Beams;
D=Ozone Chamber;
E=Electrostatic Screen;
F=Charcoal Filters w/Copper In FIG. 12 there is shown a side view of a typical device for initial activity in a dirty building environment wherein there is shown section [A] the overt UV-C saturation chamber; then an optional section [B] for Vapor from Dissolvent Acid; another optional section [C] for Laser Beams; then the Ozone Chamber [D], & a final section of filters rated long-lasting @ 6 months of charcoal & copper particles. All sections can be assembled at the onset when starting to clean up a dirty building, & removed, or replaced, when switched off, if deemed not needed.

In FIG. 13 is shown a side view of a smaller typical device with two less sections having been removed. Such a device as this one shown is designed for long term use in a building having been already cleaned down with an earlier full scale device. This view contains the all-important UV-C saturation chamber [section A] that will destroy virtually all incoming infectious materials; & displays a Laser Beam section [C] that is an option; & a likely necessary section [D] of Ozone Vapors; then passing into the section [F] of 6 long lasting replaceable filters.

In FIG. 14 is shown another side view of a device wherein the entry section [A] is of UV-C ultraviolet C type which is the most deadly item in the UV saturation chamber & will do most of the elimination work & wherein the entry intake air [34] is marked by arrows [38] into the UV-C saturation chamber & wherein UV bulbs & UV diodes [40] will obliterate every organic particulate & with dead organic material dropping down into a refuse chamber [47] for later collection by a vacuum cleaned by means of vacuum portals [48] for that purpose. Any further material faces obliteration by laser beams [46] & the Ozone Chamber [D] prior to an exit [38] clean & safe for the processed & sterilized air to the return air vent [34] to HEPA for re-circulation in the forced air ventilation system. In selected situations further cleaning may require a filtering step wherein such filters will be assembled within the exit air [34] system.

The display of this invention has now shown all necessary features & designs to eliminate the particulates & infectious material in the modern type closed window buildings that today all use the forced air ventilation system [aka HEPA]. The use of HEPA is mandated by the continual need of air changes & oxygen throughout a closed building. This invention will prove satisfactory over time to put into use, to assure good health & continued freedom of infectious material that currently sickens & kills so many patients that are currently using hospital facilities.

An additional set of features is anticipated to be optional & available when requested to be paid extra for these services. In many areas including larger cities, the electric main power can go off oftentimes from violent storms & local catastrophes. The main power can be critical to many lives & services in a hospital or office building, & so this option should be considered before such events occur.

The most inexpensive at onset would be rechargeable & replaceable batteries, today the most popular & successful item would be the Lithium-Ion Type in a replaceable pack with a unused pack near at hand. These batteries are chemical & very powerful but last 2.5 to 3 years before they die out & need replacement. The value of such optional services would include extra power outlets for other medical or service requirements without interruption.

A more expense option can be a complete self-charging system that runs on its own with a chemical Vapor Motor that does Not Use Fossil Fuel, have a Tailpipe to Pollute, uses No Oxygen, & is in a sealed tight casing to be Clean & Green. This quiet & unobtrusive power system can provide large amounts of electrical power over long periods of time. In a hospital setting many medical procedures & services can continue to be provided, even surgery & operations, with this new auxiliary electric power.

Also, a reminder that most electric power is called The Grid, & perhaps 98% of these power plants are using coal to fire up their generators to carelessly pollute, It seems interesting that The Grid when it sells you their power that they have No Production Costs in making & producing their electric power These electric plants have No Raw Material Costs as they use just Air & built-in Magnets to spin. Making electricity costs Nothing until you have it shipped into your business or home or car, A Cash Cow!

I claim:

1. A device for cleansing air of particulates and infectious material, wherein the device comprises:
   a. a casing constructed of a material that blocks radiation from leaving the device, wherein the casing has an air inlet on a first side of the casing and an air outlet on a second side of the casing;
   b. a first chamber located in the casing downstream of the air inlet, wherein the first chamber contains ultraviolet (UV) light sources that emit ultraviolet light spectrums capable of killing microorganisms in the air;
   c. a second chamber located in the casing downstream of the first chamber, wherein the second chamber contains an ozone generator capable of creating ozone gas in the second chamber;
   d. a series of filters for removing particulates from the air, wherein the series of filters is located in the casing downstream of the second chamber;
   e. a fan located in the casing for moving air through the casing; and
   f. a light emitting diode (LED) indicator that indicates when the series of filters should be replaced;
   wherein the device is mounted in a room over a return air vent of a main forced air ventilation system of a building such that air exits the device into the return air vent.

2. The device of claim 1, wherein the return air vent is completely covered by the device.

3. The device of claim 1, further comprising an acid bath located downstream of the first chamber and upstream of the second chamber, wherein the air passes through vapors released from the acid bath.

4. The device of claim 3, further comprising laser beam emitter capable of emitting a continuous laser beam array, wherein the laser beam emitter is located downstream of the acid bath and upstream of the second chamber.

5. The device of claim 4, further comprising electrostatic screens located downstream of the second chamber and upstream of the series of filters.

6. The device of claim 1, wherein the series of filters include at least one charcoal filter.

7. The device of claim 6, wherein the at least one charcoal filter includes copper particles.

8. The device of claim 1, further comprising a lithium-ion battery pack as a backup power supply to the device.

9. The device of claim 1, wherein the UV light sources are controllable by a first off/on switch and the ozone generator is controllable by a second off/on switch.

10. The device of claim 1, further comprising a first particle counting sensor located in the casing near the inlet of the casing and a second particle counting sensor located in the casing near the outlet of the casing, wherein the first and second particle counting sensors are configured to ascertain the difference of particles in the air entering the device and leaving the device.

* * * * *